(12) United States Patent
Imaizumi et al.

(10) Patent No.: US 11,828,750 B2
(45) Date of Patent: Nov. 28, 2023

(54) MATERIAL FOR SCREENING FOR COMPOUND ACTING ON ION CHANNEL AND USE THEREOF

(71) Applicants: PUBLIC UNIVERSITY CORPORATION NAGOYA CITY UNIVERSITY, Nagoya (JP); CHANNELOSEARCH TECHNOLOGY, Nagoya (JP)

(72) Inventors: Yuji Imaizumi, Nagoya (JP); Hisao Yamamura, Nagoya (JP); Yoshiaki Suzuki, Nagoya (JP); Keisuke Kawasaki, Nagoya (JP); Hiroshi Narita, Saitama (JP)

(73) Assignees: PUBLIC UNIVERSITY CORPORATION NAGOYA CITY UNIVERSITY, Nagoya (JP); CHANNELOSEARCH TECHNOLOGY, Nagoya (JP)

( * ) Notice: Subject to any disclaimer, the term of this patent is extended or adjusted under 35 U.S.C. 154(b) by 722 days.

(21) Appl. No.: 16/344,778

(22) PCT Filed: Nov. 1, 2017

(86) PCT No.: PCT/JP2017/039641
§ 371 (c)(1),
(2) Date: Jul. 10, 2019

(87) PCT Pub. No.: WO2018/084221
PCT Pub. Date: May 11, 2018

(65) Prior Publication Data
US 2019/0331664 A1    Oct. 31, 2019

(30) Foreign Application Priority Data
Nov. 1, 2016    (JP) .................................. 2016-214685

(51) Int. Cl.
*C12Q 1/02* (2006.01)
*G01N 33/50* (2006.01)
*G01N 33/68* (2006.01)

(52) U.S. Cl.
CPC ......... *G01N 33/5014* (2013.01); *C12Q 1/025* (2013.01); *G01N 33/5032* (2013.01); *G01N 33/5058* (2013.01); *G01N 33/6872* (2013.01); *G01N 2500/02* (2013.01); *G01N 2500/10* (2013.01)

(58) Field of Classification Search
CPC .. C12N 5/10; G01N 33/5014; G01N 33/6572; C12Q 1/025
See application file for complete search history.

(56) References Cited

U.S. PATENT DOCUMENTS

2013/0183709 A1    7/2013  Imaizumi et al.

FOREIGN PATENT DOCUMENTS

| JP | 2006-126073 A | 5/2006 |
| WO | 2012/002460 A1 | 1/2012 |

OTHER PUBLICATIONS

Crumb Jr. et al. J of Pharmacological and Toxicological Methods, 2016, printed as pp. 1-12.*
Fujii, Masato et al., "Development of Recombinant Cell Line Co-Expressing Mutated Nav 1.5, Kir2.1, and hERG for the Safety Assay of Drug Candidates," Journal of Biomolecular Screening, vol. 17, No. 6, 2012, pp. 773-784 and pp. 1-5.
Kawasaki Keisuke, et al., "New Screening System for Selective Modulators of K2P Channels Using Recombinant Cell Lines Dying Upon Single Action Potential," The 89th Annual Meeting of the Japanese Pharmacological Society, Mar. 11, 2016.
Fujii, Masato et al., "New Screening System for Selective Blockers of Voltage Gated K+ Channels Using Recombinant Cell Lines Dying Upon Single Action Potential," Journal of Pharmacological Scienes, vol. 123, No. 2, 2013, pp. 147-158.
Jan. 23, 2018 International Search Report issued in International Patent Application No. PCT/JP2017/039641.
Jan. 23, 2018 Written Opinion issued in International Patent Application No. PCT/JP2017/039641.

* cited by examiner

*Primary Examiner* — Bin Shen
(74) *Attorney, Agent, or Firm* — Oliff PLC

(57) ABSTRACT

A screening system provided with a potential-dependent Na ion channel that extends the duration of the action potential associated with depolarization, and a K ion channel that deepens the resting membrane potential in the negative direction, said screening system furthermore including cells provided with ion channels that contribute to deepening the resting membrane potential in the negative direction and/or shortening the duration of the action potential as target ion channels. By such cells, the action of a test compound on the target ion channel can be easily evaluated by providing an inhibitor for the K ion channel to control the probability of cell death.

4 Claims, 9 Drawing Sheets

Specification includes a Sequence Listing.

FIG. 3

K2P channels related to various diseases

| | Related Disease | Related K2p Channel | Reference |
|---|---|---|---|
| Central Nervous System | Depression | *TREK-1, TREK-2, TASK-3* | Heurteaux et al., 2006, Enyedi et al., 2010, Bayliss et al., 2008, Borsotto et al., 2015 |
| | Ischemic Heart Disease | *TREK-1, TREK-2, TASK-1,TASK-2, TASK-3* | Bayliss et al., 2008, Es-Salah-Lamoureux et al., 2010, Ehling et al., 2015, |
| | Epilepsy | *TREK-1, TREK-2, TASK-2* | Es-Salah-Lamoureux et al., 2010 |
| | Anxiety Disorders | *TASK-1* | Es-Salah-Lamoureux et al., 2010 |
| | General Anesthesia | *TREK-1, TREK-2,TASK-2* | Heurteaux et al., 2004, Franks et al., 2004 |
| | Migraine | *TRESK* | Enyedi et al., 2015 |
| | Pain | *TREK-1, TRAAK, TRESK* | Alloui et al., 2006, Honore, 2007, Noel et al., 2009, Devilliers et al., 2013 |
| Circulatory System | Hypertension | *TREK-1, TASK, TWIK-2* | Blondeau et al., 2007, Bayliss et al., 2008 |
| | Pulmonary Hypertension | *TWIK-2* | Enyedi et al., 2010, Pandit et al., 2014 |
| | Chronic Atrial Fibrillation | *TASK-1* | Schmitt et al., 2014, Schmitt et al., 2015 |
| | Hereditary Arrhythmia | *TALK-2* | Schmitt et al., 2014, Friedrich et al., 2014 |
| | Malignant Tumor | *Twik-1 (Prostate Cancer), Trek-1 (Prostate Cancer, Esophageal Squamous Cell Carcinoma), Task-3 (Breast Cancer, Lung Cancer), Thik-1 (Ductal Carcinoma, Synovial Sarcoma, Malignant Peripheral Nerve Sheath Tumor)* | Enyedi et al., 2010, Es-Salah-Lamoureux et al., 2010 |
| | Immune Diseases | *TASK-1, TASK-3, TREK-1* | Es-Salah-Lamoureux et al., 2010, Enyedi et al., 2010, Ehling et al., 2015 |
| | Azoospermia | *TALK-2, TRAAK* | Dube et al., 2008 |

RELATED ART

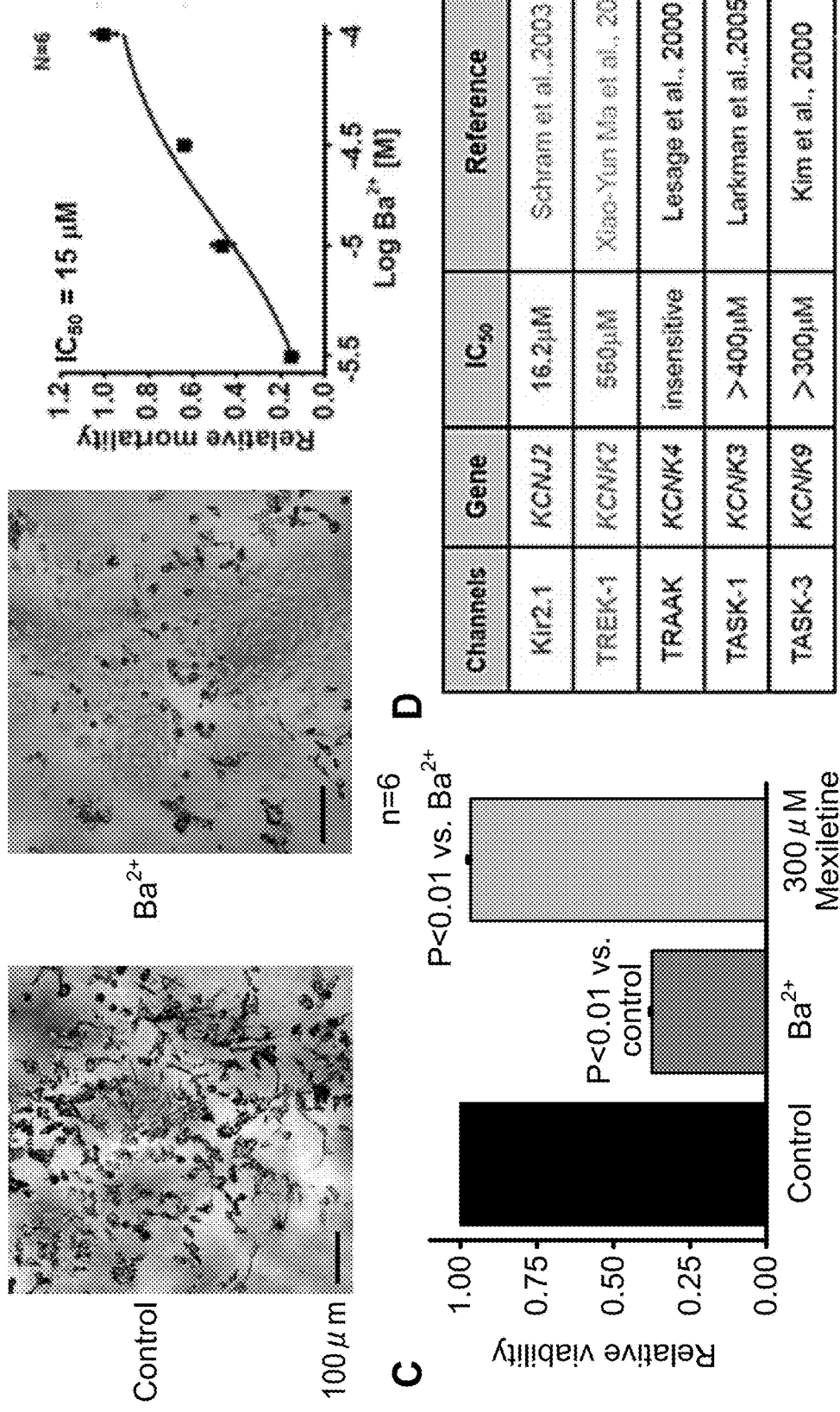
FIG. 4 Novel applications of test cells to comprehensive HTS of agents that act on K2P channels, with a focus on the extent of $Ba^{2+}$ sensitivity of Kir 2.1

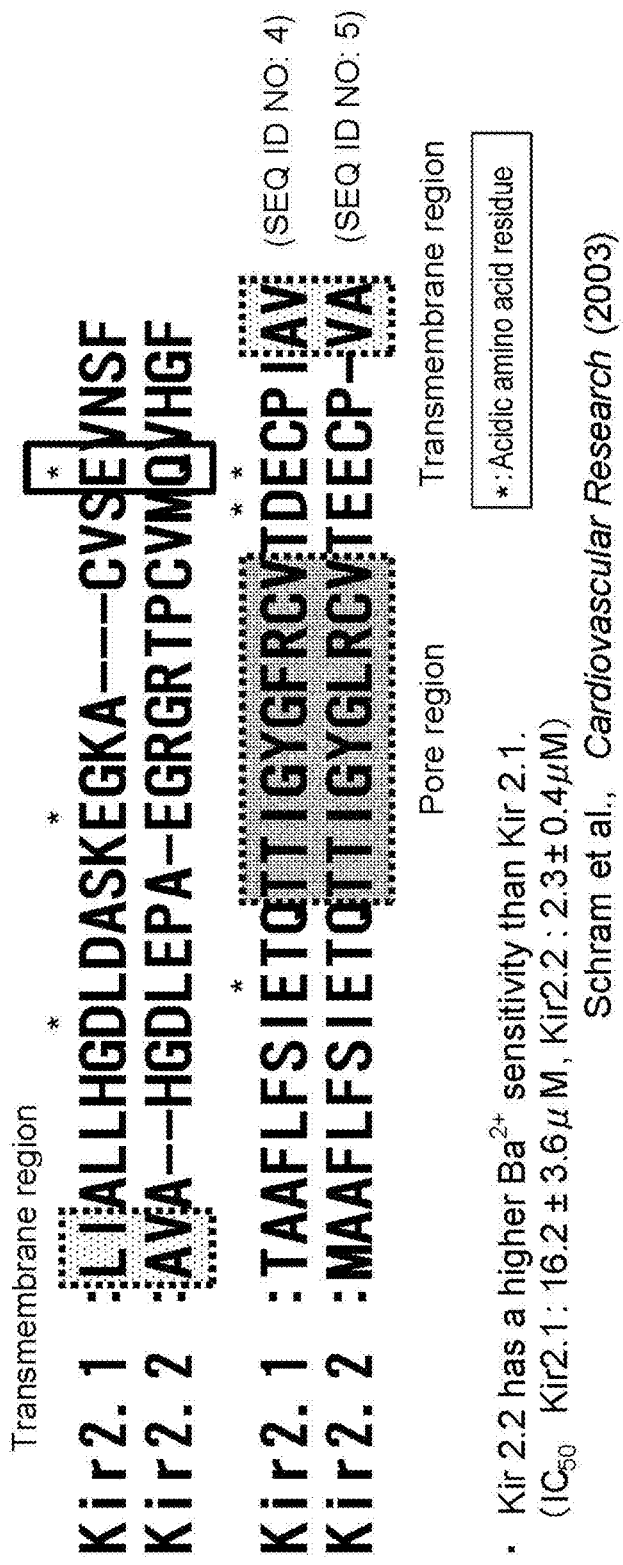

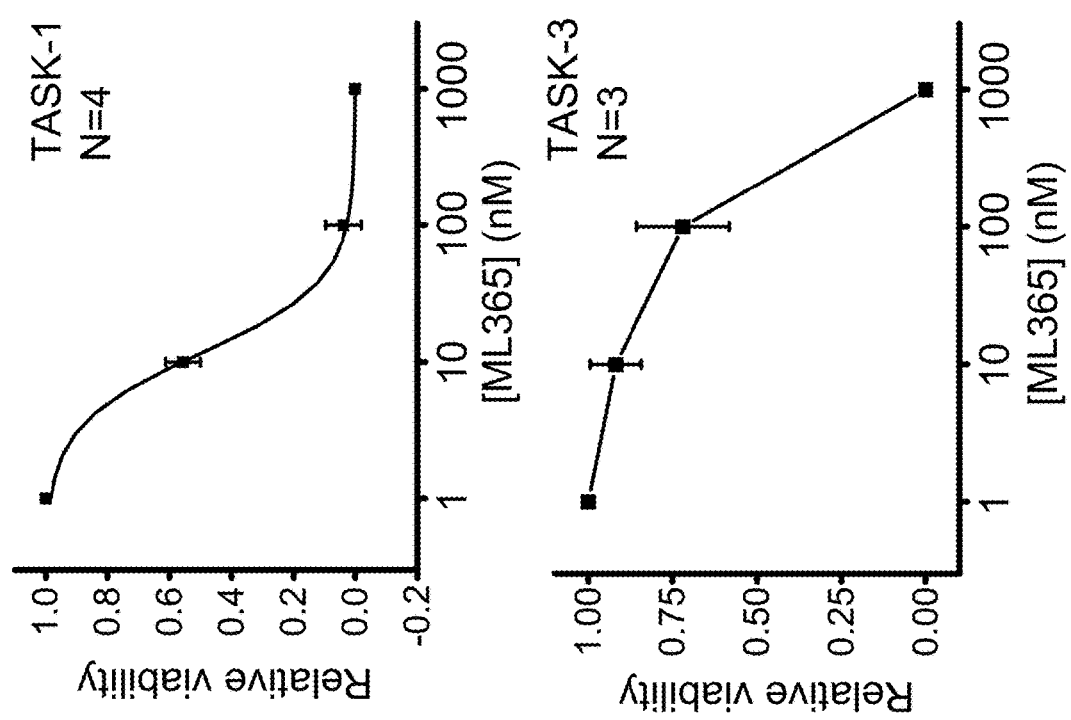
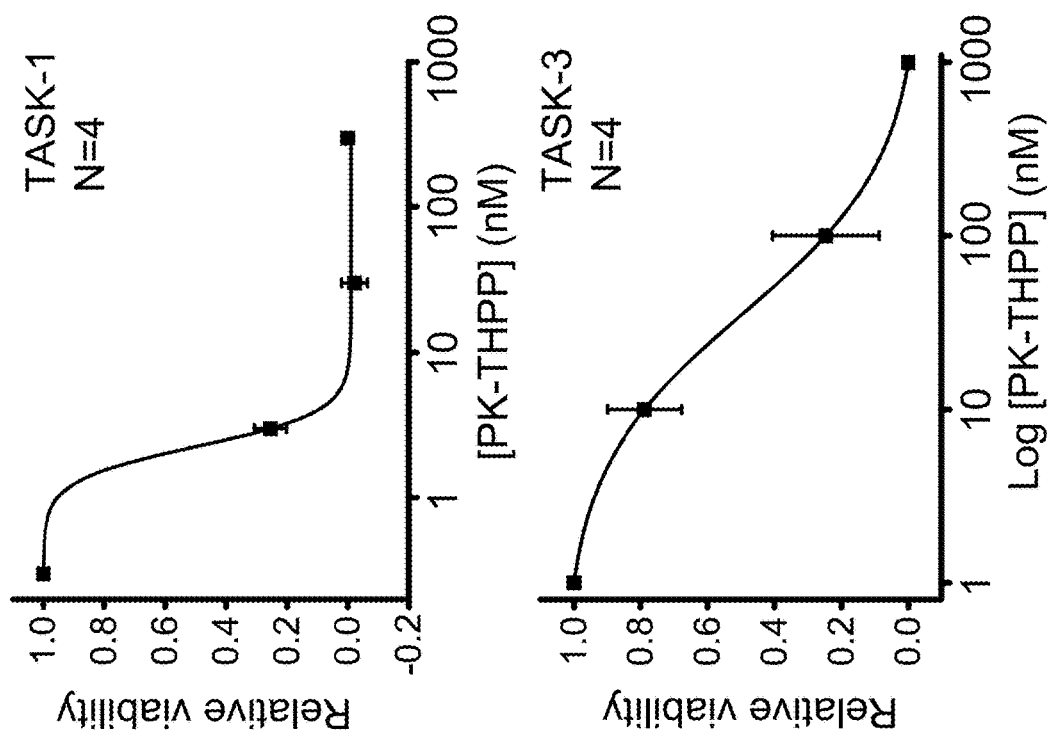
FIG. 7

MATERIAL FOR SCREENING FOR COMPOUND ACTING ON ION CHANNEL AND USE THEREOF

The present application contains a Sequence Listing that has been submitted electronically in ASCII format and is hereby incorporated by reference in its entirety. The ASCII copy, created on Jun. 14, 2022, is named Substitute_Sequence_Listing_ST25.txt and is 19,491 bytes in size.

TECHNICAL FIELD

The present Description relates to a material for screening for compounds that act on ion channels and to the use of this screening material.

BACKGROUND ART

Ion channels have physiologically important functions. The discovery of agonists and inhibitors that act on ion channels by targeting these ions channels is expected to provide useful drugs. A known example of a method for evaluating screening systems for drugs targeting such ion channels, for example, voltage-dependent ion channels, is a fluorescent membrane potential measurement method that detects changes in a membrane potential in cells with a voltage-dependent fluorescent dye (Patent Literature 1).

In addition, the present inventors have already disclosed a novel screening system with an improved method for detecting membrane potential (Patent Literature 2). This screening system uses a transformant (screening material) constructed by the introduction of a $Na^+$ ion channel (referred to simply as a Na ion channel in the following) and a $K^+$ ion channel (referred to simply as a K ion channel in the following) so as to have a cell death induction system whereby the transformant is viable in the normal state, while cell death is induced once cell depolarization is induced. One type of screening using this screening material is screening for inhibitors for a target ion channel using a depolarization stimulus. In this screening, for example, a target ion channel is introduced into and expressed by this screening material, and this screening material is then exposed to a test compound and a depolarization-inducing electrical stimulus. When the cell death of this screening material is inhibited, the test compound can be regarded as a candidate inhibitor of the target ion channel.

CITATION LIST

Patent Literature 1: Japanese Patent Application Laid-open No. 2006-126073
Patent Literature 2: WO 2012/002460

SUMMARY

However, even with the screening method according to Patent Literature 2, the screening of a test compound against a target ion channel frequently requires a process of applying an electrical stimulus in order to induce cellular depolarization. A non-general purpose electrical stimulation device is required to apply the electrical stimulation and also causes the process to be complex. The electrical stimulation process for applying depolarization thus requires both time and effort. There is therefore demand for the establishment of a screening system that may be advantageously applied to efficient large-scale screening and to primary screening.

The present Description provides a screening method that brings about a substantial improvement in the screening efficiency of a screening material that is equipped with a cell death induction system in which cell death is induced by the induction of depolarization. Use of this screening method is also provided.

Solution to Technical Problem

The present inventors focused on the K ion channel, which is one of the elements associated with the induction of depolarization, in screening systems that use a screening material provided with a cell death induction system, and focused on inwardly rectifying K ion channels in particular. This K ion channel, in previous screening materials provided with a cell death induction system, has deepened a resting membrane potential in the negative direction and has ensured cell survival by inhibiting, in the normal state, action in the direction of cell death by a voltage-dependent Na ion channel that prolongs the duration of a depolarization-induced action potential.

The present inventors discovered that, by supplying an inhibitor that exhibits a specific inhibitory action on this K ion channel, depolarization can be induced and cell death can be induced. The present inventors also discovered that, even in the presence of a K ion channel inhibitor, cell death can be suppressed in a steady state in which hyperpolarization is maintained and depolarization is not induced, by expressing as a target ion channel an ion channel that drives the resting membrane potential of the screening material in the negative direction, or by expressing as the target ion channel an ion channel that contributes to shortening the duration of the action potential. The present inventors additionally discovered that when the state of the target ion channel is changed, e.g., by supplying an agonist or inhibitor for the target ion channel in this screening material, the intracellular ionic environment changes and maintenance of hyperpolarization or induction of depolarization is produced, and these results can be detected as cell survival or cell death, respectively. The present Description provides the following based on this knowledge.

(1) A screening material for agonists or inhibitors for a target ion channel, wherein the screening material contains cells provided with
a voltage-dependent Na ion channel that prolongs the duration of an action potential associated with depolarization,
a K ion channel that deepens a resting membrane potential in the negative direction, and
a target ion channel that is an ion channel that contributes to deepening the resting membrane potential in the negative direction and/or that shortens the duration of the action potential associated with depolarization,
wherein the Na ion channel, the K ion channel, and the target ion channel constitute a cell death induction system with which cell death is induced by the induction of depolarization in the presence of an inhibitor for the K ion channel.

(2) The screening material according to (1), wherein the target ion channel has an inhibitory action on the cell death induced by the cell death induction system.

(3) The screening material according to (1) or (2), that uses a selective inhibitor of the K ion channel.

(4) The screening material according to (3), wherein the target ion channel has a lower sensitivity to the K ion channel inhibitor than the K ion channel.

(5) The screening material according to any of (1) to (4), wherein the target ion channel is an ion channel that contributes to deepening the resting membrane potential in the negative direction and is another K ion channel that is different from the aforementioned K ion channel.

(6) The screening material according to (5), wherein the another K ion channel is a K2P channel.

(7) The screening material according to any of (1) to (6), wherein the target ion channel is an ion channel that contributes to a shortening of the duration of the action potential associated with depolarization.

(8) A method for screening for an agonist or inhibitor of a target ion channel, wherein the method
uses cells provided with a voltage-dependent Na ion channel that prolongs the duration of an action potential associated with depolarization, a K ion channel that deepens the resting membrane potential in the negative direction, and a target ion channel that is an ion channel that contributes to deepening the resting membrane potential in the negative direction and/or that shortens the duration of the action potential associated with depolarization, wherein the Na ion channel, the K ion channel, and the target ion channel constitute a cell death induction system with which cell death is induced by the induction of depolarization in the presence of an inhibitor for the K ion channel,
and is provided with
a step of supplying the inhibitor to the cells;
a step of supplying the cells with a test compound having the potential to inhibit or activate the target ion channel; and
a step of evaluating the effect on cell death of the cells due to the supply of the test compound.

(9) A kit for screening for an agonist or inhibitor of a target ion channel, the kit being provided with
cells provided with a voltage-dependent Na ion channel that prolongs the duration of an action potential associated with depolarization, a K ion channel that deepens the resting membrane potential in the negative direction, and a target ion channel that is an ion channel that contributes to deepening the resting membrane potential in the negative direction and/or that shortens the duration of the action potential associated with depolarization, wherein the Na ion channel, the K ion channel, and the target ion channel constitute a cell death induction system with which cell death is induced by the induction of depolarization in the presence of an inhibitor for the K ion channel, and
the inhibitor.

BRIEF DESCRIPTION OF DRAWINGS

FIG. 3 is a diagram that shows K2P channels that are related to various diseases. The ion channels given in italics indicate ion channels for which an inhibitor (blocker) provides a drug effective for treatment, while ion channels not given in italics indicate ion channels for which an agonist (opener) provides a drug effective for treatment;

FIG. 4 is a diagram that shows the results of an evaluation of the action of the $Ba^{2+}$ ion (referred to below simply as the Ba ion) on K2P channel-nonexpressing cells;

FIG. 5 is a diagram that shows an example of the production of a K ion channel mutant that has a high Ba ion sensitivity;

FIG. 7 is a diagram that shows dose-response curves for PK-THPP and ML365, which are TASK-1 and TASK-3 inhibitors, for cells expressing TASK-1 or TASK-3 (both are a type of K2P channels);

DESCRIPTION OF EMBODIMENTS

The present Description relates to a screening material targeted to ion channels. The present Description more specifically relates to a screening material comprising cells that can be used to screen for compounds that act on ion channels (membrane transport proteins), to a screening method that uses this material, and to a screening kit.

For screening in which the indicator is cell death brought about by an agent for a target ion channel, a system must be constructed in which survival occurs in the steady state in which depolarization is not induced, while cell death is achieved when depolarization is induced. Electrical stimulation is required in order to induce depolarization in the cell death induction system-equipped cells already disclosed by the present inventors, i.e., cells in which the duration of the depolarization-induced action potential is prolonged, but which, in a state in which depolarization is not being induced, are rendered viable by a deepening of the membrane potential in the negative direction.

The present inventors have now discovered for the first time that the cell death induction system itself possessed by these cells can also be used as a system that can induce depolarization. In other words, the present inventors have discovered that a mechanism that can control depolarization and cell death without an electrical stimulus can be made inherent in the previous cell death induction system itself. The present inventors have additionally discovered that, by using as the target ion channel an ion channel that enables a suppression of depolarization not induced by electrical stimulation, a novel cell death induction system (evaluation system) can be constructed that enables the facile evaluation of the action of a test compound on this type of target ion channel (also referred to in the following as an inhibitory target ion channel). An overview of the present screening material is shown in FIG. 1.

Figure 1:
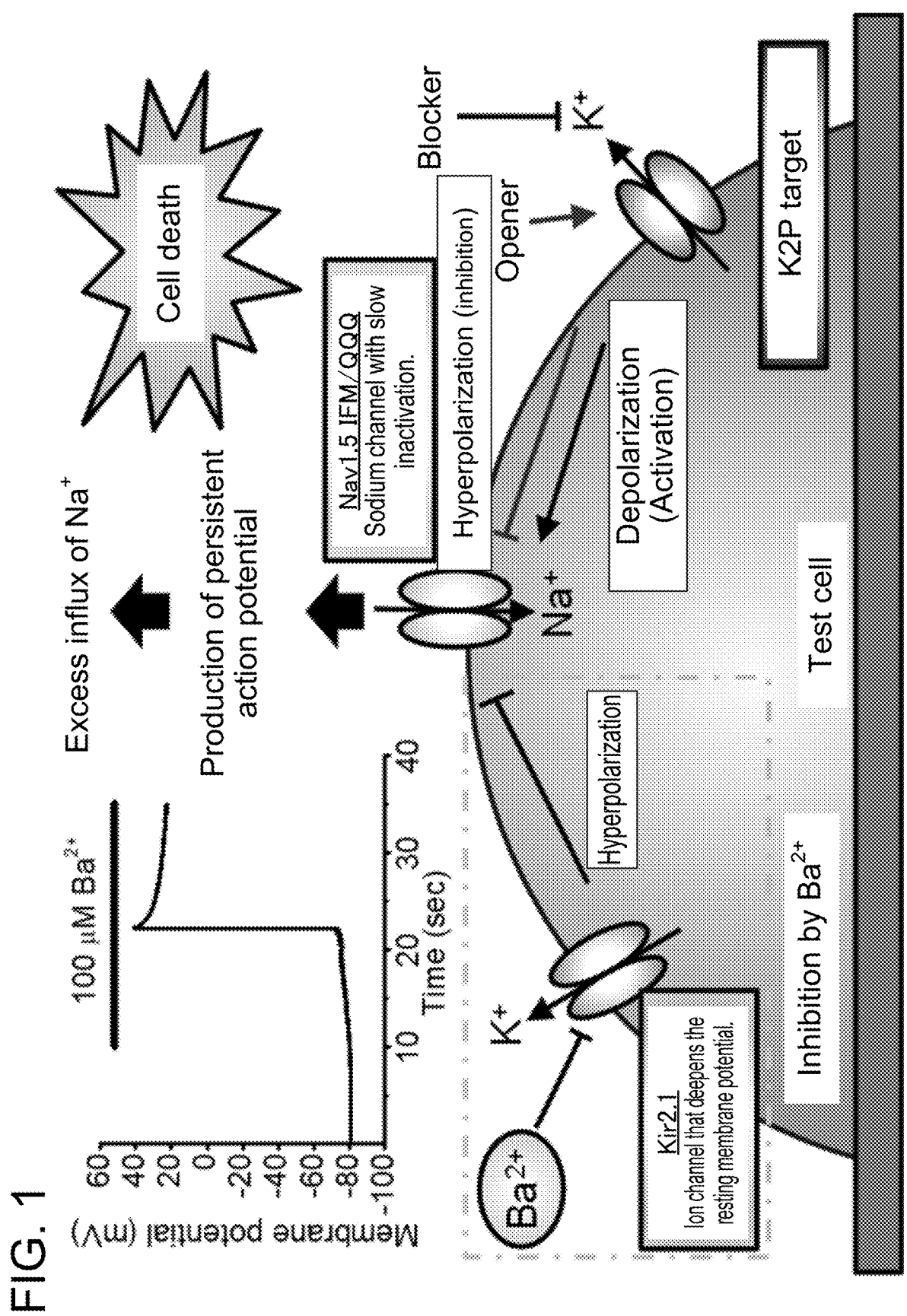
FIG. 1 is a drawing that shows an overview of a screening material disclosed in the present Description.

FIG. 1 shows, for the present screening material, a system in which survival occurs in the steady state where depolarization is not induced, while cell death is achieved when depolarization is induced. As shown in FIG. 1, the present screening material is provided with a Na ion channel that prolongs the duration of the action potential generated in association with depolarization, and with a K ion channel that deepens the resting membrane potential. The present screening material is also provided with an inhibitory target ion channel, which is an ion channel that contributes to deepening the resting membrane potential in the negative direction and/or to shortening the duration of the action potential associated with depolarization. This Na ion channel, K ion channel, and inhibitory target ion channel constitute a cell death induction system in which cell death is induced in the presence of an inhibitor of the K ion channel by the induction of depolarization, i.e., constitute an evaluation system for evaluating action on the inhibitory target ion channel in the presence of an inhibitor of the K ion channel.

In FIG. 1, for example, Nav 1.5 IFM/QQQ is used for the Na ion channel; Kir 2 is used for the K ion channel; and a K2P ion channel is used for the inhibitory target ion channel.

In this screening material, through the action on the K ion channel of an agent that inhibits the K ion channel, for example, the Ba ion, the action of the K ion channel in the direction of deepening the resting membrane potential is inhibited, the induction of depolarization is facilitated, and the screening material is strongly biased toward cell death. On the other hand, through the expression of an inhibitory target ion channel that inherently acts to inhibit the depolarization due to this inhibitor, the inhibitor-induced depolarization is suppressed and the cell death bias of the screening material is also suppressed. The cells are viable as a result. Here, when an agent that inhibits the action of the inhibitory target ion channel, for example, an inhibitor (blocker), is supplied to the screening material, the inhibitory bias on cell death exercised by the inhibitory target ion channel is then suppressed and a strong bias toward cell death is established for the screening material and cell death is induced. In addition, when an agent that promotes the action of the target ion channel, for example, an agonist (opener), is supplied, the inhibitory bias on cell death by the inhibitory target ion channel is either retained or promoted, and as a consequence cell death is not induced in the screening material.

Figure 2:
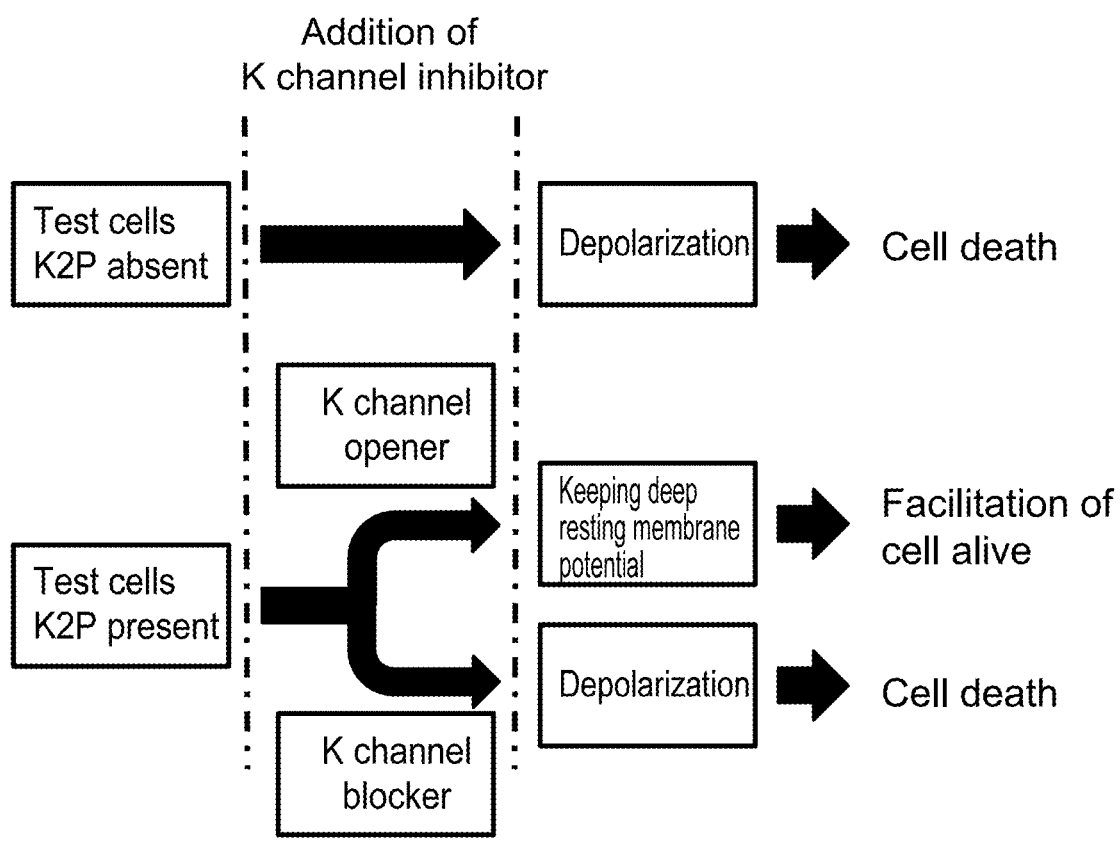
FIG. 2 is a drawing that shows the action, in accordance with the screening art disclosed in the present Description, of an opener (agonist) and a blocker (inhibitor) on the target ion channel, for example, a 4-pass transmembrane and 2-pore K ion channel (K2P channel)

FIG. 2 shows a comparison of the present screening material, which is provided with a Na ion channel, a K ion channel, and an inhibitory target ion channel, with cells provided with a Na ion channel and a K ion channel, with regard to the action of an opener (agonist) and a blocker (inhibitor) on the inhibitory target ion channel, for example, a K2P channel.

As shown in FIG. 2, when an inhibitor of the K ion channel is supplied to a cell not provided with an inhibitory target ion channel, an ion channel that exercises inhibitory control on depolarization is either not present or exhibits a low activity, and as a consequence the resting membrane potential of the cell membrane is no longer maintained and depolarization is induced and cell death is thereby induced.

When, on the other hand, an opener (agonist) for the inhibitory target ion channel is supplied in the presence of the K ion channel inhibitor to the present screening material, which is constituted of cells provided with the inhibitory target ion channel, activation of the inhibitory target ion channel results in maintenance of the resting membrane potential of the cell membrane, or changes it in the direction of hyperpolarization, and as a consequence depolarization is not induced, cell death is not induced, and the cell survives. In contrast to this, when a blocker (inhibitor) for the inhibitory target ion channel is supplied, the inhibitory bias on cell death due to the inhibitory target ion channel is cancelled, a strong bias for cell death is established in the screening material, and cell death is induced.

Thus, for the screening material shown in FIG. 2, the fate of the cell, i.e., cell survival/cell death, is ultimately determined by whether, or to what degree, the resting membrane potential is maintained.

Thus, the present screening material disclosed in the present Description is provided with a Na ion channel and a K ion channel that constitute a cell death induction system, but is also provided with a target ion channel that exercises an inhibitory action on the depolarization in this induction system. As a consequence, using the induction of depolarization brought about by supplying the cells with an inhibitor of the K ion channel, the action of an agent on the inhibitory target ion channel can be evaluated and screening for inhibitors or agonists can then be carried out.

The preceding description concerns the use, for the inhibitory target ion channel, of an ion channel that deepens the resting membrane potential in the negative direction; however, the inhibitory target ion channel also includes ion channels that shorten the duration of the action potential associated with depolarization. That is, the screening material may also be provided with an inhibitory target ion channel in the form of an ion channel that shortens the duration of the action potential associated with depolarization. Ion channels that deepen the resting membrane potential in the negative direction are at the same time also ion channels that shorten the duration of the action potential associated with depolarization. When an opener (agonist) for the inhibitory target ion channel is supplied to screening material provided with an inhibitory target ion channel in the form of an ion channel that shortens the duration of the action potential associated with depolarization, the shortening of the duration of the action potential is maintained and cell death is again not induced and the cell survives. When, on the other hand, a blocker (inhibitor) for the inhibitory target ion channel is supplied, shortening of the duration of the action potential is then no longer maintained by the inhibitory target ion channel, and the duration is either maintained or prolonged and cell death is induced.

Thus, for this screening material, the fate of the cell, i.e., cell survival/cell death, is ultimately determined by whether, or to what degree, the duration of the action potential is shortened.

With the screening material disclosed in the present Description, the cell death percentage in the screening material can be adjusted using the concentration of the inhibitor for the K ion channel. As a consequence, for example, by causing an inhibitor to be present at an inhibition ratio at which 50% of the cells die and supplying a test compound to the screening material, the test compound can be evaluated qualitatively and quantitatively as both an opener (agonist) or blocker (inhibitor) for the target ion channel.

The screening material disclosed in the present Description enables an efficient screening by providing an evaluation system that is constructed to contain a target ion channel and that uses a K ion channel inhibitor and the action on this target ion channel.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved material for screening for compounds that act on ion channels and to the use of this screening material.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

In the present Description, an ion channel agonist refers to an agent (e.g., a compound or protein) that maintains or promotes the intrinsic function of an ion channel of interest. In addition, an ion channel inhibitor refers to an agent (e.g., a compound or a preparation of biological origin) that at least partially inhibits the intrinsic function of an ion channel of interest.

(Screening Material) The present screening material is provided with a voltage-dependent Na ion channel that prolongs the duration of the action potential associated with depolarization. The present screening material is also provided with a K ion channel that deepens the resting membrane potential in the negative direction. The present screening material is further provided with a target ion channel that is an ion channel that contributes to deepening the resting membrane potential in the negative direction and/or that shortens the duration of the action potential associated with depolarization.

There are no particular limitations on the cells in the present screening material provided they can be used for ion channel screening, and various types of animal and plant cells can be used. Examples of animal cells include mammalian cells and insect cells, although there are no particular limitations thereon. In the case of cells other than human cells, such as bovine, porcine, equine, ovine, goat, avian, canine, feline, or rabbit cells, screening material used to screen for drugs for the prevention or treatment of diseases in these animals can be acquired. When the host is an insect cell, screening material used to screen, e.g., pesticides, targeted to insects, can be acquired. When plant cells are used for the cells, screening material used to screen, e.g., agricultural chemicals, can be acquired. Examples of animal cells that are typically used include human embryonic kidney cells (HEK cells), African green monkey cells (COS cells), Chinese hamster ovary cells (CHO cells), baby hamster kidney cells (BHK cells), and African clawed frog oocytes. Cultured cells derived from various tissue types may also be used.

(Na Ion Channel) The Na ion channel provided in the present screening material is a voltage-dependent Na ion channel that prolongs the duration of the action potential associated with depolarization. In other words, this Na ion channel may also be referred to as a deactivation-inhibited Na ion channel.

Here, the voltage-dependent Na ion channel is a protein on the cell membrane that mediates passive diffusion of the Na ion by a cell membrane potential-dependent opening. There are no particular limitations on the voltage-dependent Na ion channel used in the present Description and various known voltage-dependent Na ion channels can be used; however, a Nav 1.5 channel is preferred. The Nav 1.5 channel is distributed in, e.g., myocardial cells, and is thought to be involved with generation of the action potential and the conduction of excitation.

A voltage-dependent Na ion channel exhibits Na ion permeability by a gate opening that depends on the membrane potential, after which a deactivation mechanism operates and the Na ion permeability is lost (deactivation). In contrast, this deactivation mechanism is inhibited (lost) in a deactivation-inhibited voltage-dependent Na ion channel. That is, a deactivation-inhibited voltage-dependent Na ion channel refers to a Na ion channel in which this deactivation is not produced after the appearance of the ion permeability due to membrane potential-dependent gate opening. With a deactivation-inhibited voltage-dependent Na ion channel, when the ion channel itself is activated by the induction of depolarization in the cell membrane, the ion channel opens and a state is assumed that can mediate passive diffusion of the Na ion; however, because deactivation of the ion channel itself has been inhibited, the open state of the ion channel is maintained. As a result, with a deactivation-inhibited voltage-dependent Na ion channel, when stimulation has been received and once an action potential has been generated, deactivation of the ion channel is delayed and as a consequence the action potential continues for longer than for the original voltage-dependent Na ion channel.

In addition, a deactivation-inhibited Na ion channel is either constantly easily activated or is easily activated at a relatively deep resting membrane potential (the so-called window current is large). Thus, in cells expressing such a Na ion channel, the influx of excess Na ion can be prevented only when the resting membrane potential is maintained at a sufficiently deep negative potential. In cells that adequately express such a voltage-dependent Na ion channel, Na ion channel activation is easily increased by depolarization and the action potential or depolarization is maintained for about 1 minute or more, preferably 2 minutes or more, more preferably 3 minutes or more, and even more preferably 5 minutes or more. As a consequence, an excess Na influx into the cell is produced and causes cell death.

This inhibition of deactivation can be suitably realized by inserting an amino acid mutation into the amino acid sequence of a voltage-dependent Na ion channel. Several specific techniques have been disclosed for inhibiting deactivation of the Nav 1.5 channel. Examples of reported techniques include modifying the IFM motif (Grant et al., Biophys. J., 79:3019-3035, 2000), mutation of the asparagine at position 406 to glutamic acid, arginine, or lysine (McNulty et al., Mol. Pharmacol., 70:1514-1523, 2006), deletion of a linker site containing an IFM motif that connects domains III and IV (Patton et al., Proc. Natl. Acad. Sci. USA, 89:10905-10909, 1992, West et al., Proc. Natl. Acad. Sci. USA, 89:10910-10914, 1992), and mutation of an amino acid of segment 4 of domain IV (Chen et al., J. Gen. Physiol., 108:549-556, 1996). Insertion of a mutation into an amino acid sequence can be suitably carried out by a person having ordinary skill in the art based on these documents and common general technical knowledge.

The present screening material preferably expressibly retains DNA (also referred to as a first DNA in the following) that encodes such a Na ion channel (natural protein or mutant protein). The present screening material may constantly or transiently express this mutant, i.e., the deactivation-inhibited voltage-dependent Na ion channel. In other words, this DNA may be incorporated in a chromosome so as to be transmitted to a daughter cell, or may be incorporated in a plasmid that is autonomously amplified extrachromosomally and is not necessarily transmitted to a daughter cell. The DNA is preferably linked under the control of a constantly active promoter (constitutive promoter). This screening material can be suitably acquired as constantly expressing cells or transiently expressing cells by constructing, e.g., a DNA-containing expression vector and then inserting same into and transforming a screening material host based on genetic engineering technology and transformant production technology commonly known among persons having ordinary skill in the art.

In addition, the amount of expression for the Na ion channel can be adjusted by controlling, e.g., the type of control region, e.g., promoter and so forth, that controls the first DNA, the number of first DNA-containing expression cassettes inserted, and the cell culture conditions post-insertion.

Furthermore, in the case that the voltage-dependent Na ion channel is composed of two or more subunits, and when subunits containing mutations effective for deactivation only constitute a portion of the entirety thereof, DNA respectively encoding those subunits can be expressed in the screening material in the form of one or two or more DNAs, or DNA encoding these subunits may be respectively and expressibly retained as DNA such that other subunits composing the Na ion channel are simultaneously co-expressed. Moreover, if there are, e.g., enzymes, other proteins, compounds, and so forth required for the expressed deactivation-inhibited voltage-dependent Na ion channel to function more effectively, these substances may also be suitably expressed or supplied.

(K Ion Channel That Deepens Resting Membrane Potential in Negative Direction)

The K ion channel placed in the present screening material is an ion channel that exhibits the function (activity) of deepening the resting membrane potential in the negative direction, i.e., of making the potential more negative. That is, a deep resting membrane potential can be formed due to an enhanced K ion permeability brought about by the expression and activity of this K ion channel. When the aforementioned Na ion channel is provided, a state is assumed in which, due to the intra-versus-extracellular concentration difference for the Na ion, excess Na ion flows into the cell, ultimately resulting in the intracellular Na ion concentration increasing and cell death. In order to use the cells as a screening material, the cells must be viable until this cell death induction system is induced. A K ion channel that deepens the resting membrane potential in the negative direction is therefore used in order to deepen (lower) the resting membrane potential.

The resting membrane potential is preferably deepened in the negative direction to a degree that does not affect cell viability. The membrane potential is preferably −50 mV, more preferably −60 mV, even more preferably about −70 mV, and still more preferably about −80 mV.

Such a K ion channel may be, for example, a state in which an inwardly rectifying K ion channel (Kir channel) or a 4-pass transmembrane and 2-pore K ion channel (K2P channel) is activated. There are various types of 4-pass transmembrane and 2-pore K ion channels (K2P channels) having different properties, and these are classified into, for example, TWIK, TREK, TASK, TALK, THIK, TRESK, and so forth. These ion channels exhibit almost no dependence on potential or time and thus function as leak channels. Based on their properties as leak channels, these K ion channels function to maintain (fix) the resting membrane potential of the cell.

Although there are no particular limitations on the inwardly rectifying K ion channel, examples include various types of Kir 2x channels such as Kir 2.1, 2.2, 2.3, and 2.4.

Kir 2.1 is an inwardly rectifying K ion channel (Kir channel) that has a 2-pass transmembrane structure. This channel is not dependent on voltage and its membrane potential has the property of approaching around −80 mV, which is the K ion equilibrium potential. This channel is expressed in nerves and heart and skeletal muscle and carries out the formation of the resting membrane potential along with its stabilization and maintenance. Kir 2.2 is, like Kir 2.1, an inwardly rectifying K ion channel (Kir channel), but has a more potent inward rectification than Kir 2.1. It is expressed with Kir 2.1 in, e.g., the heart and brain and skeletal muscle, and plays a leading role in inwardly rectifying K ion channel (Kir channel) activity in human vascular endothelial cells. In addition, Kir 2.2 is advantageous for the present screening material in that it is selectively inhibited by, for example, the Ba ion as described below.

The Kir 2.x ion channels are described in, for example, Circ. Res. 94:1332-1339 (2004) and Am. J. Physiol. Cell Physiol. 289:C1134-C1144 (2005). Examples of base sequences for genes encoding human-derived Kir 2.x channels include Kir 2.1 (GenBank Accession No. U12507, NM #000891(Human KCNJ2)), Kir 2.2 (GenBank Accession No. AB074970, NM #021012 (Human KCNJ12)), Kir 2.3 (GenBank Accession No. U07364, U24056, NM #152868 (Human KCNJ4)), and Kir 2.4 (GenBank Accession No. AF081466 NM #013348 (Human KCNJ14)).

The G protein-coupled inwardly rectifying K ion channel (GIRK channel, Kir) is similarly an example. The GIRK channel (Kir 3) is an inwardly rectifying K ion channel (Kir channel) which, differing from Kir 2, is a G protein-activated K ion channel. Subunits thereof are tissue-specific, and form heterogeneous tetramers composed of Kir 3.1/Kir 3.4 in the heart and Kir 3.1/Kir 3.2 in the central nervous system. They are normally not activated and are activated by agonist stimulation. However, it has been reported according to experiments using African clawed frog oocytes that these ion channels are brought into a constantly open state by the mutation of amino acids in the transmembrane helix that forms the ion channel pores (Claydon et al., J. Biol. Chem., 278:50654-50663, 2003). On the basis of this finding, the use of this mutant is thought to enable the formation of a deep resting membrane potential in the same manner as Kir 2.1. Examples of base sequences that encode human-derived Kir 3.x channels include Kir 3.1 (GenBank Accession No. NM #002239 (Human KCNJ3)), Kir 3.2 (GenBank Accession No. NM #002240 (Human KCNJ6)), Kir 3.3 (GenBank Accession No. NM #004983 (Human KCNJ9)), and Kir 3.4 (GenBank Accession No. NM #000890 (Human KCNJ5)).

Moreover, another example is the ATP-sensitive inwardly rectifying K ion channel ($K_{ATP}$ channel, Kir 6). The $K_{ATP}$ channel is an inwardly rectifying K ion channel (Kir channel) that is inhibited by ATP and activated by ADP. The $K_{ATP}$ channel controls cell excitability in conformity to the metabolic state of the cell. The $K_{ATP}$ channel is a heterogeneous octamer composed of four $K_{ATP}$ channels and four sulfonylurea receptors (SUR). Although the $K_{ATP}$ channel alone does not have a function, the $K_{ATP}$ channel alone has been reported to have a function when the C terminal of the $K_{ATP}$ channel is deleted (Tucker et al., EMBO J., 17:3290-3296, 1998). In addition, this deletion variant can be made to be constantly activated by decreasing the ATP sensitivity by the introduction of additional mutation. The use of this mutant also enables the formation of a deep resting membrane potential. Examples of base sequences encoding human-derived Kir 6.x channels include Kir 6.1 (GenBank Accession No. NM #004982 (Human KCNJ8)) and Kir 6.2 (GenBank Accession No. NM001166290 (Human KCNJ11)).

In addition, known examples of 4-pass transmembrane and 2-pore K ion channels (K2P channels) include the THIK channel (in which the membrane potential becomes deeper when expressed in HEK293 cells; Campanucci et al., Neuroscience, 135:1087-1094, 2005), the TASK2 channel (in which the resting membrane potential becomes deeper when expressed in African clawed frog oocytes; Kindler et al., J. Pharmacol. Exp. Ther., 306:84-92, 2003), and the voltage-dependent K channel (the voltage-dependent K channel deepens the resting membrane potential in smooth muscle tissue; McDaniel et al., J. Appl. Physiol. (1985), 91:2322-2333, 2001).

4-pass transmembrane and 2-pore K ion channels (K2P channels) are classified into their respective subfamilies consisting of TWIK, TREK, TASK, TALK, THIK, and TRESK. The TWIK subfamily includes the TWIK-1 and TWIK-2 channels (Lotshaw, Cell Biochem. Biophys. 47:209-256, 2007). TWIK channels are present in numerous tissues in humans. Examples of human-derived TWIK ion channels include TWIK-1 (GenBank Accession No. NM #002245 (KCNK1)) and TWIK-2 (GenBank Accession No. NM #004823 (KCNK6)).

The TREK subfamily includes the TREK-1, TREK-2, and TRAAK channels. Examples of human-derived TREK ion channels include TREK-1 (GenBank Accession No. NM #014217 (KCNK2)), TREK-2 (GenBank Accession No. NM #138317 (KCNK10)), and TRAAK (GenBank Accession No. NM #033310 (KCNK4)).

The TASK subfamily includes the TASK-1, TASK-3, and TASK-5 channels. Examples of human-derived TASK ion channels include TASK-1 (GenBank Accession No. NM #002246 (KCNK3)), TASK-3 (GenBank Accession No. NM #016601 (KCNK9)), and TASK-5 (GenBank Accession No. NM #022358 (KCNK15)).

The TALK subfamily includes the TALK-1, TALK-2, and TASK-2 channels. Examples of human-derived TALK ion channels include TALK-1 (GenBank Accession No. NM #001135106 KCNK16)), TALK-2 (GenBank Accession No. NM #001135111 (KCNK17)), and TASK-2 (GenBank Accession No. NM #003740 (KCNK5)).

The THIK subfamily includes the THIK-1 and THIK-2 channels. Examples of human-derived THIK ion channels include THIK-1 (GenBank Accession No. NM #022054 (KCNK13)) and THIK-2 (GenBank Accession No. NM #022055 (KCNK12)).

Examples of the TRESK subfamily include TRESK (GenBank Accession No. NM #181840 (KCNK18)).

In addition to these various natural K ion channels, a K ion channel mutant provided by their modification may also be used as the K ion channel. The present screening material is advantageously used in the presence of a K ion channel inhibitor. This inhibitor preferably can inhibit the K ion channel with the highest possible selectivity and at the highest possible sensitivity (at a low concentration). Accordingly, appropriate modifications may be introduced into the K ion channel in order to endow the K ion channel with a more favorable selectivity and/or sensitivity to inhibitors.

For example, in the alignment of the amino acid sequence of Kir 2.2 with the amino acid sequence of Kir 2.1 as shown in FIG. 5, it is thought that a favorable Ba ion sensitivity is obtained by substituting the Q (glutamine) in the Kir 2.2 amino acid sequence, which corresponds to E125 in Kir 2.1, with an acidic amino acid residue, e.g., E (glutamic acid) or aspartic acid (D). Various regions of Kir channel proteins, e.g., transmembrane regions, pore regions, and so forth, have already been identified (e.g., Scharm et al., Cardiovasc. Res. 59:328-338, 2003). In addition, E125 of Kir 2.1 is also already known to assist interaction between the Ba ion and Kir channels (Alagem et al., J. Physiol. 534:381-393, 2001).

Art for modifying known proteins in order to, e.g., provide or abolish a function of interest, or enhance or weaken same, is known to the person having ordinary skill in the art. With regard to a protein of interest and particularly, e.g., ion channels, it is a common task for the person having ordinary skill in the art to thoroughly research, e.g., a transmembrane region or pore region, and then identify to a certain extent suitable modifiable sites by using alignment of the protein amino acid sequences. It is also a common task for the person having ordinary skill in the art to acquire mutants considering potential amino acid residue substitutions based on the alignment data for modifiable sites and to evaluate the functionality of the mutants.

In the present screening material, one or a suitable combination of two or more of these K ion channels may be used for the purpose of deepening the resting membrane potential.

As for the Na ion channel, the present screening material preferably expressibly retains DNA (also referred to in the following as a second DNA) that encodes the aforementioned K ion channel (natural protein or mutant protein). The present screening material may constantly or transiently express a natural or mutant K ion channel. Namely, this DNA may be incorporated in a chromosome so as to be transmitted to a daughter cell, or may be incorporated in a plasmid that is autonomously amplified extrachromosomally and is not necessarily transmitted to a daughter cell. As for the first DNA, the second DNA is also preferably linked under the control of a constantly active promoter (constitutive promoter). The same embodiments as for the Na ion channel are used when the K ion channel is composed of two or more different subunits. The amount of K ion channel expression may also be adjusted in the same manner as for the first DNA.

The present screening material, because it is provided with the aforementioned Na ion channel and the aforementioned K ion channel on, e.g., the cell membrane, thus takes the form of cells that, even though they have a mutant deactivation-inhibited voltage-dependent Na ion channel, avoid the cell death caused by Na ion inflow into the cell, until depolarization is induced. Namely, while a cell death induction system is present, the cell death induction system resides in a standby state awaiting the induction of depolarization to operate.

(Inhibitory Target Ion Channel) The inhibitory target ion channel that can be incorporated in the present screening material is an ion channel that contributes to deepening the resting membrane potential in the negative direction and/or that shortens the duration of the action potential associated with depolarization. The inhibitory target ion channel can act to inhibit the induction of depolarization or induction of cell death that is brought about by an inhibitor (also referred to hereafter as a K ion channel inhibitor) that acts to inhibit the K ion channel provided in the present screening material and can thereby induce cell death by inducing depolarization in the cell death induction system. The inhibitory target ion channel can, independently of this inhibitor, inhibit the action of the inhibitor, i.e., can inhibit the induction of depolarization or the induction of cell death due to the induction of depolarization. The selection of such an ion channel makes it possible to construct an efficient system for evaluating this ion channel.

(K Ion Channel Inhibitor) The K ion channel inhibitor inhibits the action of the K ion channel and thus inhibits the deepening of the resting membrane potential in the negative direction. This inhibitor also varies, for example, with the type of K ion channel. K ion channel inhibitors may be acquired based on known information, but they may also be acquired by preparing cells that are provided with a cell death induction system containing any of various K ion channels, supplying a potential K ion channel inhibitor to these cells, and evaluating whether the induction of depolarization or the induction of cell death has occurred.

For example, the Ba ion is known to be an inhibitor of Kir 2.x. The other elements in the present evaluation system, for example, the Nav 1.5 Na ion channel or mutant thereof and K2P channel used as a target ion channel, infra, preferably have a low sensitivity to the Ba ion. More specifically, the 50% inhibitory concentration for the ion channels other than the K ion channel of the cell death induction system is preferably at least 5-times higher, more preferably at least 7-times higher, even more preferably at least 10-times higher, still more preferably at least 15-times higher, and much more preferably at least 20-times higher than the 50% inhibitory concentration for the K ion channel of the cell death induction system. By having such a selective inhibition be present, the action of a test compound on the inhibitory target ion channel can be detected and evaluated with high sensitivity. This inhibitory concentration and the like can also be measured using cells provided with the cell death induction system disclosed in the present Description.

For the inhibitory target ion channel, an ion channel is selected that, in the presence of an inhibitor of the K ion channel in the cell death induction system, can inhibit the induction of cell death by this inhibitor. A criterion for selection may be that the 50% inhibitory concentration by the K ion channel inhibitor is, for example, sufficiently higher than that for said K ion channel (also referred to hereinafter as a first K ion channel), or that the action of the inhibitor with respect to the first K ion channel can be suppressed. Besides the 50% inhibitory concentration, the presence/absence of the ability to inhibit cell death by suppressing the action of the inhibitor with respect to the first K ion channel may also be evaluated by expressing various potential target ion channels in the cell death induction system already described in the preceding.

The inhibitory target ion channel should be an ion channel that contributes to deepening the resting membrane potential in the negative direction and/or to shortening the duration of the action potential associated with depolarization, and is selected as appropriate from the various known ion channels in conformity to the type of K ion channel in the cell death induction system and/or the inhibitor used for same.

The species of ion for the inhibitory target ion channel can be exemplified by the Na ion, K ion, $Ca^{2+}$ ion (referred to hereafter simply as the Ca ion), the $Cl^-$ ion (referred to hereafter simply as the Cl ion), and so forth. Examples of ion channels include voltage-dependent channels, ligand-dependent channels, mechanical stimulation-dependent channels, temperature-dependent channels, leak channels, and phosphorylation-dependent channels depending on the manner of control of the opening and closing thereof. According to the disclosure of the present Description, since action (activation or inhibition) on the inhibitory target ion channel can be detected through the survival or death of the screening material, a wide range of ion channels in general can be used as the inhibitory target ion channel. Furthermore, in the present Description, an ion channel is referred to regardless of the manner of control of the opening and closing thereof, whether it be a voltage-dependent ion channel or ligand-dependent ion channel and the like. In addition, ion channels include transporters, ion exchangers (such as $Na^+$—$Ca^{2+}$ exchangers), and ion pumps (such as $Na^+$—$K^+$ pumps) in biomembranes including nuclear membranes and cell membranes engaged in voltage-generating ion transport as well as other intracellular organelle membranes and the like. Through the selection of the target ion channel for the screening material, a screening material for the prevention or treatment of disease associated with said target ion channel can be provided.

The target ion channel can be exemplified first of all by various types of ion channel-integrated drug receptors. Examples of these receptors include nicotinic acetylcholine receptors, ion channel-type ATP receptors (P2X receptors), ion channel-type glutamate receptors, ion channel-type γ-aminobutyric acid ($GABA_A$) receptors, ion channel-type glycine receptors, and type 3 serotonin receptors. In addition, other examples include various types of transient receptor potential (TRP) channels (non-selective positive ion channels). Other examples include store-operated Ca ion channels constituted of, for example, Orai and STIM molecules. In addition, other examples of target ion channels include various types of voltage-dependent ion channels. Examples thereof include all voltage-dependent Ca ion channels, all voltage-dependent K ion channels (including hERG channels), all voltage-dependent Na ion channels, and all voltage-dependent Cl ion channels. Furthermore, other examples include ligand-dependent Ca ion channels, Na ion channels, proton ion channels, K ion channels such as calcium-dependent (Ca ion-activation) K ion ($K_{Ca}$) channels, and Cl ion channels. Moreover, additional examples include all ion channels that open and close by sensing a stimulus such as potential, temperature, pH, tension, osmotic pressure, volume, signaling molecules, and so forth.

A target ion channel intimately related to a disease or symptoms is preferable for the target ion channel. Examples of such Na ion channels include the Nav 1.1 to 1.3 and Nav 1.5 to 1.9 ion channels. These ion channels are related to epilepsy, neuropathic pain, arrhythmia, and pain, and can be used to screen for drugs used to treat or prevent these conditions. In addition, examples of Ca ion channels include Cav 1.1, 1.2, 1.3, 1.4, 2.1, 2.2, 2.3, 3.1, 3.2, and 3.3. These ion channels are related to cardiovascular disease, Alzheimer's disease, pain, epilepsy, and hypertension, and can be used to screen for drugs used to treat or prevent these conditions. Examples of K ion channels include Kv 1.1 to 1.5, 2.1, 3.2, 4.3, 7.1 to 7.5, 10.1, 11.1 (including hERG), 12.1 to 12.3, and SK. These ion channels are related to multiple sclerosis, autoimmune diseases, pain, atrial fibrillation, diabetes, epilepsy, neuralgia, Alzheimer's disease, urinary incontinence, arrhythmia, and cancer, and can be used to screen for drugs used to treat or prevent these conditions. In addition, with regard to Cl ion channels, CLC-1, 5, 7, Ka, and Kb are related to, e.g., myotonia, kidney disease, metabolic bone disease, and hypertension, and can be used to screen for drugs used to prevent or treat these conditions.

For example, an hERG K ion channel is preferable for the target ion channel. This ion channel is one of the voltage-dependent K ion channels that has a 6-pass transmembrane structure and forms a tetramer. One of the differences between this K ion channel and other voltage-dependent K ion channels is that this K ion channel demonstrates inward rectification. This is attributable to the extremely rapid occurrence of C-type inactivation. This K ion channel also acts strongly in the repolarization phase, which is the third phase of the action potential of the heart. This K ion channel is known to be strongly involved in cancer and also arrhythmia since it has an action that causes hyperpolarization of the membrane potential in the repolarization phase. Since highly fatal long QT syndrome is induced when hERG K ion channels are inhibited, currently all types of drug candidate compounds are required to be assessed for a proarrhythmia action attributable to cardiotoxicity stemming from inhibitory action on hERG K ion channels. Consequently, a screening material having an hERG K ion channel for the target ion channel is highly useful. In the case of expression of an hERG K ion channel in the screening material, since an action potential generated by, for example, an electrical stimulus, is shortened, cell death is unlikely. By adding a compound that is known to have or suspected to have an inhibitory action on hERG K ion channels, cell death occurs more easily in the screening material depending on the degree of that inhibition, thereby making it possible to quantitatively evaluate inhibitory effects on hERG K ion channels. An example of hERG is GenBank Accession No. NM #000238.

The already described inwardly rectifying K ion channels (Kir channels), K ion channels that contribute to deepening (fixing) the resting membrane potential, and Cl ion channels are suitable for the inhibitory target ion channel. K ion channels are ion channels that by opening lead the cell in the direction of hyperpolarization and that by closing inhibit same. Cl ion channels are ion channels that by opening lead the cell in the direction of depolarization and that by closing inhibit same. K ion channels in the role of the inhibitory target ion channel are referred to as the second ion channel in order to distinguish them from the K ion channel that is the target of action for the inhibitor. The second ion channel can be exemplified by the K2P channels, Kv channels, Kir channels, and so forth already described above for the K ion channel. The Cl ion channel can be exemplified by CLC channels.

4-pass transmembrane and 2-pore K ion channels (K2P channels) are particularly suitable among the preceding. K2P channels are currently regarded as promising targets for drug discovery for, e.g., anti-pain drugs, anti-inflammatory drugs, and anticancer drugs. As shown in FIG. 3, 17 types of K2P channels are currently known. In FIG. 3, those for which a therapeutic or prophylactic effect on the disease can be expected for an inhibitor (blocker) are indicated with italics, while those for which a therapeutic or prophylactic effect on the disease can be expected for an agonist (opener) are indicated with normal type.

The K2P channels are ion channels that form the resting membrane potential and are known to have a Ba ion sensitivity that is well below (for at least, at least 20-times, at least 30-times, and so forth) that of Kir 2.x and are advantageous also for having a low Ba ion sensitivity. The various K2P ion channels given in FIG. 3 are particularly suitable, and the TREK ion channels, e.g., TREK-1, TASK ion channels, e.g., TASK-1 and TASK-3, and TRAAK ion channel are more suitable from the standpoint of Ba ion sensitivity.

Besides the K2P channels and Kir channels, for example, Ca ion-activated K ion ($K_{Ca}$) channels and ATP-dependent K ion channels are also suitable for the inhibitory target ion channel. This is also because these are inhibitory ion channels that deepen the resting membrane potential.

For example, the Ca ion-activated K ion channels include a big conductance Ca ion-activated potassium (BK) channel and a small conductance Ca ion-activated potassium (SK) channel and, with a conductance between these, an intermediate conductance Ca ion-activated potassium (IK) channel. The SK channel can be exemplified by the SK1, SK2, and SK3 channels. The SK2 channel is a small conductance calcium-activated potassium channel type 2 (SK2, KCNN2, $K_{Ca}2.2$), while the IK channel is otherwise named SK4 (KCNN4, $K_{Ca}3.1$). SK1, SK2, SK3, and IK (SK4) are calcium-activated potassium channels that belong to the same class genetically, although IK (SK4) has a somewhat larger potassium ion permeability ($K^+$ conductance) than SK1, SK2, and SK3.

For example, SK2 and SK4 are one type of calcium-activated K ion channel, and are K channels that belong to a family different from that of the K2P channels. As with the K2P channels, agents that act on the SK channel can be evaluated by expressing an SK channel as an inhibitory target ion channel in the screening material. SK channels are strongly activated by supplying, in the presence of an activator (for example, the already known DCEBIO or NS309), the $Ca^{2+}$ ionophore ionomycin in order to raise the intracellular $Ca^{2+}$ concentration. As a consequence, depolarization is not induced and cell death is not induced even when the Kir 2.X in the screening material is inhibited by the addition of $Ba^{2+}$. In contrast, when an SK channel blocker (inhibitor) is added and supplied, the inhibition of cell death is suppressed and as a result cell death is induced in the screening material. This method may be used to evaluate both activators and inhibitors.

The present screening material should be functionally equipped with such an inhibitory target ion channel. The present screening material preferably specifically expresses or strongly expresses the inhibitory target ion channel. This results in a screening that has a better accuracy and sensitivity. Since ion channels are frequently distributed into specific cells, cells strongly expressing the ion channel to be targeted can also be selected in advance as parent cells for the screening material. In addition, in order to express a target ion channel in the screening material, the screening material preferably expressibly retains DNA encoding the target ion channel (third DNA). Preferably the third DNA is linked under the control of a constantly acting promoter (constitutive promoter) and the inhibitory target ion channel is constantly expressed. For the inhibitory target ion channel also, as already described the desired constantly expressing or transiently expressing cells may be acquired as appropriate by constructing, e.g., an expression vector containing the third DNA and then effecting transformation by its insertion into a screening material host, based on genetic engineering technology and transformant production technology commonly known among persons having ordinary skill in the art.

With the present screening material, a system of cell death induction in the presence of a K ion channel inhibitor (the cells are in a viable state on standby for a cell death-inducible state) can be constructed by the provision of the aforementioned Na ion channel, the aforementioned K ion channel, and the aforementioned inhibitory target ion channel. This cell death induction system itself constitutes a system for evaluating agonists and inhibitors for the inhibitory target ion channel. That is, a state is assumed in which the deepening of the resting membrane potential in the negative direction is inhibited by the presence of an inhibitor for the K ion channel, while the induction of depolarization is inhibited by the inhibitory target ion channel. An efficient evaluation can be conveniently carried out from this state of the inhibitory action or promoting action of test compounds on the inhibitory target ion channel.

(Screening Method) The screening method disclosed in this Description (also referred to herebelow as the present screening method) is a method for screening for agonists and inhibitors for a target ion channel. The present screening method can be provided with a step of supplying a K ion channel inhibitor to the present screening material so as to inhibit the action of the K ion channel; a step of supplying the present screening material with a test compound having the potential to inhibit or activate the inhibitory target ion channel; and a step of evaluating the effect of this supply of the test compound on cell death in the present screening material. The action of the test compound on the inhibitory target ion channel can be conveniently evaluated with the present screening material by supplying a K ion channel inhibitor and thereby inhibiting the K ion channel. For example, depolarization can be induced in the screening material without the use of electrical stimulation. An efficient screening is made possible as a result.

Moreover, because the action due to the K ion channel is inhibited by the K ion channel inhibitor while the cell death induction system is also controlled by the inhibitory target ion channel, which inhibits the cell death induction action due to the K ion channel inhibitor, by adjusting the K ion channel inhibitor concentration a favorable screening environment can be constructed in accordance with the properties of the test compound of interest, i.e., whether it is an inhibitor or agonist for the inhibitory target ion channel. For example, by supplying the K ion channel inhibitor in such a manner that the cell death percentage is lower than 50%, an environment favorable for screening inhibitors of the inhibitory target ion channel can be constructed. In addition, by supplying the K ion channel inhibitor in such a manner that the cell death percentage exceeds 50%, an environment favorable for screening agonists of the inhibitory target ion channel can be constructed.

Moreover, by, for example, supplying the K ion channel inhibitor in such a manner that the cell death percentage is around 50%, a qualitative and quantitative evaluation can be carried out of whether the test compound for the target inhibitory ion channel is an inhibitor or an agonist.

For example, if the Ba ion is supplied at a concentration that yields a cell death percentage of around 50%, the cell death percentage is then lowered from around 50% when a K2P channel opener is present, i.e., the percentage of cells remaining alive is increased from around 50%. When, on the other hand, a K2P channel blocker is present, the cell death percentage is increased from around 50%, i.e., the percentage of cells remaining alive is reduced from around 50%. Using this procedure, the action (agonist or inhibitor) on the inhibitory target ion channel of a test compound can be detected and evaluated using cell death/cell viability for the screening material, i.e., using the cell mortality ratio (or survival ratio).

When carrying out screening, one or two or more test compounds can be supplied to the screening material. The action of a test compound may be detected using a single test compound, or the combined action, additive action, or synergistic action of two or more test compounds may be detected using these compounds. In the detection of the action on an inhibitory target ion channel based on cell death (percentage) in the screening material, cell death (percentage) in the screening material in the absence of test compound supply can be used as a control group. In addition, a compound with a known action on the inhibitory target ion channel may be used as a control group. The presence or absence of an action by a test compound on the inhibitory target ion channel, or the degree of that action, can be detected by comparison with such control groups.

There are no particular limitations on the test compound. In addition to low molecular weight compounds, the test compound may be, for example, a protein, peptide, nucleic acid (DNA or RNA) such as an oligonucleotide or polyoligonucleotide, oligosaccharide, polysaccharide, or lipid.

Various types of stimuli may be applied to the screening material as necessary in addition to a test compound. This is because action may be promoted or inhibited by combination with these stimuli. In addition, the action on a target ion channel that is activated or deactivated in the presence of a stimulus can also be evaluated. Examples of such stimuli include temperature changes (high temperature or low temperature), pH changes, changes in $O_2/CO_2$ concentration, changes in osmotic pressure, and changes in volume.

The mode of the screening method for the present screening method is selected as appropriate in conformity with the type of the target ion channel. More specifically, the mode is selected as appropriate in conformity with the control method or function for the target ion channel. For example, the presence/absence of stimulus in order to activate (or inactivate) the target ion channel and/or the type of stimulus is selected in conformity with the control method for the target ion channel (voltage dependence, ligand dependence, mechanical stimulation dependence, temperature dependence, leak channel, phosphorylation dependence, and so forth). In addition, the evaluation mode (agonistic or inhibitory for the target ion channel) using cell death (percentage) as an indicator is selected in conformity to the function of the target ion channel. For example, when the target ion channel is a voltage-dependent ion channel, various types of functions are known to be expressed by activation (activation by a prescribed membrane potential). Specific examples thereof include generation of an action potential and conduction of excitation (associated with Na ion channels); release of neurotransmitters and generation of action potentials in nerves and cardiac muscle (associated with Ca ion channels); maintenance of membrane potential, control of excitability, and repolarization of action potential (associated with K ion channels); and membrane potential stabilization, control of excitability, ion transport, and regulation of cell volume (associated with Cl ion channels).

When, in the present screening method, the inhibitory target ion channel is an ion channel, such as a leak channel, that inhibits depolarization of and/or an action potential in (promotes hyperpolarization), e.g., the cell membrane of the screening material, an example of the mode of the evaluation step is as follows. Namely, the action of a test compound is evaluated in the presence of the test compound and a K ion channel inhibitor by using viability or death of the screening material as an indicator. In this case, in the absence of the test compound, the target ion channel is constantly activated and depolarization is inhibited or the action potential is inhibited. Consequently, an action potential is not generated or prolonged even in the presence of a K ion channel inhibitor. As a result, the screening material is viable. On the other hand, when the test compound and a K ion channel inhibitor are applied to the screening material, cell death in the screening material is promoted. When this mode is exhibited, the test compound can then be regarded as an inhibitor that has an inhibitory action on the target ion channel.

In addition, when the target ion channel is an ion channel, such as an hERG K ion channel, that upon activation inhibits depolarization of and/or an action potential in (promotes hyperpolarization) a biomembrane such as the cell membrane of the screening material, an example of the screening mode in the evaluation step is as follows. Namely, the action of a test compound is evaluated in the presence of the test compound and a K ion channel inhibitor by using viability or death of the screening material as an indicator. More specifically, when cell death in the screening material is inhibited when a K ion channel inhibitor is supplied at the same time as or after the application of the test compound to the screening material, the test compound can then be regarded as an agonist that activates the target ion channel. On the other hand, when cell death in the screening material has been promoted, the test compound can be regarded as an inhibitor that inhibits the target ion channel.

As has been described above, according to the present screening method, by using a K ion channel inhibitor, screening for agonists and inhibitors of a target ion channel can be conveniently carried out using viability or death in the screening material as an indicator. The present screening method is also suitable for screening systems requiring rapid results as well as for screening for ion channel-targeting drugs having a complex structural design, and particularly for primary screening requiring high throughput.

(Evaluation Method) The present screening method may also be executed as a method for evaluating the action of a test compound on a target ion channel. According to the present evaluation method, the action of a test compound on a target ion channel (activation or inhibition) can be measured both easily and rapidly. Thus, the present evaluation method is useful as a rapid and convenient evaluation method in those cases where at least a certain action is required of a test compound. The various types of modes for the already described present screening method can be used directly in the present evaluation method.

(Screening Kit) The kit disclosed in the present Description is a kit for screening for agonists or inhibitors of a target ion channel (also referred to herebelow as the present kit). The present kit can be provided with the present screening material and an inhibitor that inhibits the action of a K ion channel. The present kit enables the facile and efficient execution of screening for compounds that act on a target ion channel. In addition to the present screening material and inhibitor, the present kit may also be provided with a reagent for measuring cell death. The present kit may also be provided with a culture medium suitable for the present screening material. The present kit may also be provided with a compound that controls the expression and/or activity of a target ion channel and/or with equipment such as a device for electrical stimulation carried out on an optional basis. The present kit may also be used as a kit for evaluating the action of a test compound on a target ion channel.

(Method for Screening for K Ion Channel Inhibitors) The present Description also discloses a method for screening for K ion channel inhibitors (also referred to herebelow as the inhibitor screening method). According to the inhibitor screening method, screening can be carried out for an advantageous inhibitor of a K ion channel in the present screening material, i.e., screening can be carried out for a more specific and more sensitive inhibitor of the K ion channel that is used.

The inhibitor screening method can be provided with, for example, a step of preparing the cells that are provided with the Na ion channel and K ion channel in the present screening material and supplying these cells with a test compound that is a candidate inhibitor of the K ion channel, and a step of evaluating the inhibitory action of the test compound on the K ion channel by the detection of cell death or a cellular condition that can be regarded as cell death. The inhibitor screening method enables facile screening for inhibitors that even at low concentrations can inhibit the K ion channel used. An advantageous inhibitory concentration can also be acquired for an inhibitor, as can the 50% inhibitory concentration (concentration for a 50% cell mortality). The screening cells disclosed in Patent Literature 2 by the present inventors may be used as such in this inhibitor screening method. In addition, with regard to the detection of cell death or a cellular condition that can be regarded as cell death, the related modes in Patent Literature 2 may also be used as such.

The inhibitor screening method can be provided, for example, with a step of preparing, for the present screening material, test cells that are provided with a Na ion channel and a K ion channel as a test K ion channel, and supplying a K ion channel inhibitor to these cells, and a step of evaluating the inhibitory action of the inhibitor on the test K ion channel in the test cells by the detection of the death of these cells or a cellular condition that can be regarded as cell death.

By preparing test cells respectively provided with various K ion channels, this inhibitor screening method enables facile screening for inhibitors that exhibit a high specificity for a specific test K ion channel. This inhibitor screening method may also use the various modes disclosed in Patent Literature 2 by the present inventors. In particular, when a K ion channel (second K ion channel) is used as the inhibitory target ion channel, and by using a candidate inhibitory target ion channel for the test K ion channel, screening can be carried out for inhibitors having a high and specific sensitivity at the first K ion channel and a low sensitivity at the second K ion channel.

For example, the method for screening for K ion channel inhibitors can be carried out using the following mode. Thus, the culture medium is replaced by a measurement buffer and a candidate K ion channel inhibitor is added as the test compound to, for example, Kir 2.1_ion channel#mutated Nav-expressing cells. K ion channel inhibitor screening may then be carried out by incubating the cells for approximately 12 hours under conditions of 37° C., atmospheric pressure, and 5% $CO_2$ and monitoring cell death. For example, FIG. 4B gives the dose-response curve for the Ba ion (added as $BaCl_2$), which is a Kir 2.1 inhibitor, when Kir 2.1 is adopted for the K ion channel. The composition of the measurement buffer (unit=mM) can be 137 NaCl, 5.9 KCl, 2.2 $CaCl_2$, 1.2 $MgCl_2$, 14 glucose, and 10 HEPES (pH 7.4 with NaOH).

(Method for Screening Inhibitors and Activators for Na Ion Channel) The present Description also discloses a method for screening inhibitors and activators for the Na ion channel. This is because an inhibitor that inhibits the action of a voltage-dependent Na ion channel that prolongs the duration of the action potential associated with depolarization, as well as an activator that activates this action, are both useful in the screening system disclosed in this Description for, e.g., agents that act on a target ion channel.

The inhibitor screening method can be carried out using the following mode. Thus, the culture medium is replaced by a measurement buffer and 200 µM Ba ion (added as $BaCl_2$) and a Na ion channel candidate inhibitor as the test compound are added to, for example, Kir 2.1 #mutated Nav-expressing cells. This is followed by incubation of the cells for approximately 12 hours under conditions of 37° C., atmospheric pressure, and 5% $CO_2$. It is thought that cell death is inhibited when the test compound is a candidate inhibitor.

The method for screening for activators can be carried out, for example, using the following mode. Thus, the culture medium is replaced by a measurement buffer and an activator candidate compound is added as the test compound to, for example, Kir 2.1 #mutated Nav-expressing cells. This is followed by incubation of the cells for approximately 12 hours under conditions of 37° C., atmospheric pressure, and 5% $CO_2$. It is thought that cell death is induced when the test compound is an activator.

EMBODIMENTS

Examples embodying the disclosure of the present Description are described in the following, but the disclosure of the present Description is not limited thereto.

First Embodiment (Production of IFM Motif Mutant of Nav 1.5 Channel Deactivation Site)

The hydrophobic amino acid sequence Ile-Phe-Met (IFM motif) present in the III-IV linker region that controls deactivation of the Nay 1.5 channel was entirely mutated to Gln. The amino acid sequence (motif) following mutation is shown below.

hNav 1.5 Amino Acid Sequence (only the region containing IFM targeted for mutation is shown) (SEQ ID NO: 1)
1470-IDNFNQQKKKLGGQD
IFMTEEQKKYYNAMKK-1500

(The underlined IFM is mutated to QQQ)

A deactivation mutant Nay 1.5 IFM/QQQ was produced by using as template pcDNA3.1/Nav 1.5 obtained by subcloning human-derived Nav 1.5 (GenBank Accession No.: NM #198056.) in pcDNA3.1(+) (Invitrogen Corp.), and using the specific PCR primers indicated below and a Quik Change Site-Directed Mutagenesis Kit (Stratagene Corp.). The DNA sequence of the resulting clone was confirmed using the Big Dye Terminator Ver. 3.1 Cycle Sequencing Kit (Applied Biosystems Inc.) and a fluorescent capillary sequencer (ABI Prism 3100 Avant Genetic Analyzer, Applied Biosystems Inc.), and plasmid DNA was purified in large volume using a PureLink Hipure Plasmid Maxiprep Kit (Invitrogen Corp.).

```
Primers
                                        (SEQ. ID: 2)
5'-GTTAGGGGGCCAGGACCAACAACAGACAGAGGAGCAGAAG-3'

(SEQ. ID: 3)
5'-CTTCTGCTCCTCTGTCTGTTGTTGGTCCTGGCCCCCTAAC-3'
```

Second Embodiment (Cell Culture and Gene Insertion) Human-derived embryonic kidney cells (HEK293 cells) were purchased from the Health Sciences Research Resource Bank (HSRRB). 10% fetal bovine serum (FBS, Gibco Corp.) was added thereto followed by culturing at 37° C. in 5% $CO_2$ in Dulbecco's Modified Eagle Medium (D-MEM, Wako Pure Chemical Industries, Ltd.) containing 100 U/ml penicillin (Wako Pure Chemical Industries, Ltd.) and 100 µg/ml streptomycin (Meiji Seika Kaisha, Ltd.). pcDNA3.1/Kir 2.1, obtained by subcloning human-derived Kir 2.1 (NM #000891) in pcDNA3.1(+) (Invitrogen Corp.), was inserted using Lipofectamine 2000 (Invitrogen Corp.) followed by culturing in medium obtained by adding 0.2 mg/ml Zeocin (Invitrogen Corp.) to the above-mentioned D-MEM medium and then cloning Zeocin resistant cells to prepare Kir 2.1 constantly expressing cells (HEK#Kir). In addition, the deactivation mutant Nav 1.5 IFM/QQQ was inserted into the Kir 2.1 constantly expressing cells using the same method (HEK#Kir#mutated Nav).

Proceeding as above, hTREK-1#Kir 2.1 #mutated Nay cells (referred to herebelow as TREK-1 test cells) were prepared by subcloning hTREK-1 (GenBank Accession Number: NM #001017424), a type of human-derived K2P channel, in pcDNA3.1(+) and inserting it in the previously prepared Kir 2.1 #mutated Nav cells.

Figure 6:
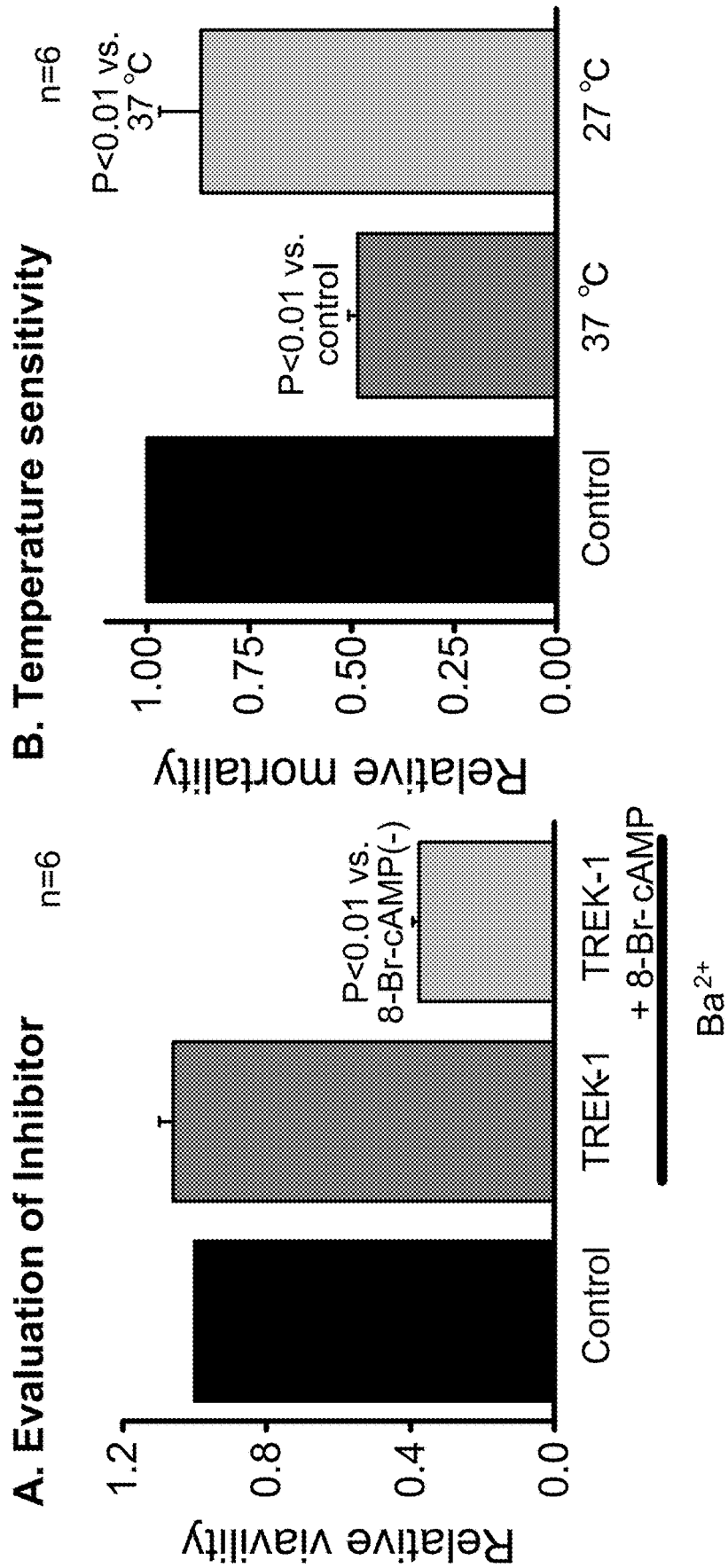
FIG. 6 is a diagram that shows, for cells that express TREK-1 (one type of K2P channel), cell death due to a TREK-1 inhibitor in the presence of the Ba ion and the temperature dependence of TREK-1.

With the TREK-1 test cells, the culture medium was replaced with measurement buffer (137 mM NaCl, 5.9 mM KCl, 2.2 mM $CaCl_2$, 1.2 mM $MgCl_2$, 14 mM glucose, 10 mM HEPES (pH 7.4 with NaOH), this also applies in the following) and $BaCl_2$ was added to provide 200 µM Ba ion, a Kir 2.1 inhibitor. This was followed by incubation for approximately 12 hours under conditions of 37° C., atmospheric pressure, and 5% $CO_2$ and monitoring of cell death. Cell death was observed when 8-Br-cAMP, a TREK-1 inhibitor, was supplied. The measurement of cell death was carried out using the MTT method with reference to a paper by the present inventors (Yamazaki, D., et al., Am J Physiol Cell Physiol 300, C75-86, 2011). The results are given in FIG. 6.

As shown in FIG. 6A, cell death was not produced when Ba ion was also supplied to the TREK-1 test cells at a total amount of 200 µM; however, cell death was produced when the TREK-1 inhibitor was supplied in the presence of the Ba ion. As shown in FIG. 6B, cell death was also induced by reducing the culture temperature to 27° C. This was regarded as being due to the temperature sensitivity of TREK-1 (Maingret et al., EMBO J., 19, 2483-2491, 2000). That is, this was considered to be due to the following: at room temperature (27° C.) TREK-1 has a low activity and thus also has a weak inhibitory effect on cell death; at a higher temperature (37° C.), TREK-1 is activated and thus has a significantly higher inhibitory effect on cell death than at room temperature.

Third Embodiment hTASK-1 (the Δi20 mutant was used due to poor transfer to the cell membrane by the wild type, resulting in the problems of a small current and measurement difficulties. This mutant is reported to readily transfer to the membrane. Renigunta et al., Traffic 7:168-181, 2006) and hTASK-3 (GenBank Accession Number: NM #001282534), which are types of human-derived K2P channels, were subcloned in a baculovirus vector, a viral vector, and were inserted into the Kir 2.1 #mutated Nav cells prepared in Second Embodiment to prepare hTASK-1 transiently expressing TASK-1#Kir 2.1 #mutated Nav cells and hTASK-3 transiently expressing hTASK-3#Kir 2.1 #mutated Nav cells (referred to herebelow as TASK-1 test cells and TASK-3 test cells), respectively, which transiently expressed hTASK-1 and hTASK-3. Sf-900 III SFM (Thermo Fisher Scientific) was used for the culture medium for baculovirus vector production, and Dulbecco's Modified Eagle Medium (D-MEM) culture medium supplemented with 10% fetal bovine serum (FBS) was used as the culture medium for the test cells.

For the TASK-1 test cells and TASK-3 test cells, the culture medium was replaced with the measurement buffer, and cell death was not produced even upon the addition of $BaCl_2$ so as to provide 200 µM Ba ion. On the other hand, as shown in FIG. 7A, the induction of cell death in a dose-dependent regime was observed when TK-PHPP, a TASK-1 and TASK-3 selective inhibitor, was added in the presence of the same amount of Ba ion. The $IC_{50}$ value for TK-THPP was, respectively, 2.36 nM and 34.7 nM. For TASK-3 this was the same as the literature value of 35 nM (Coburn et al., Chem Med Chem., 7(1), 123-33, 2012).

As shown in FIG. 7B, cell death was observed in a concentration-dependent regime also for the use of ML365, which is a selective inhibitor of TASK-1 (Flaherty et al., Bioorg Med Chem Lett., 15; 24(16):3968-3973, 2014). A sharp increase in the induction of cell death occurred from the point at which 11.5 nM was exceeded for the TASK-1 test cells and from the point at which 100 nM was exceeded for the TASK-3 test cells. The reported $IC_{50}$ values for ML365 for TASK-1 and TASK-3 are, respectively, 12 nM and 480 nM (Zou et al., Probe Reports from the NIH Molecular Libraries Program, 2010). It was thus demonstrated that the same results as for the patch clamp technique are obtained using the TASK-1 test cells and TASK-3 test cells.

Fourth Embodiment

Three types of TASK-3 test cells were prepared by carrying out insertion into the Kir 2.1#mutated Nav cells prepared in Second Embodiment using the baculovirus, i.e., the viral vector in which the hTASK-3, a type of human-derived K2P channel, was subcloned, in a range up to 3-times (2.5%, 5%, or 10% of the culture medium) the amount of introduction according to Third Embodiment. Ba ion was supplied 24 hours after viral infection followed by submission to the cell death test.

The Ba ion was supplied in accordance with Third Embodiment to these three types of TASK-3 test cells and cell death was monitored. The results are shown in FIG. 8.

Figure 8:
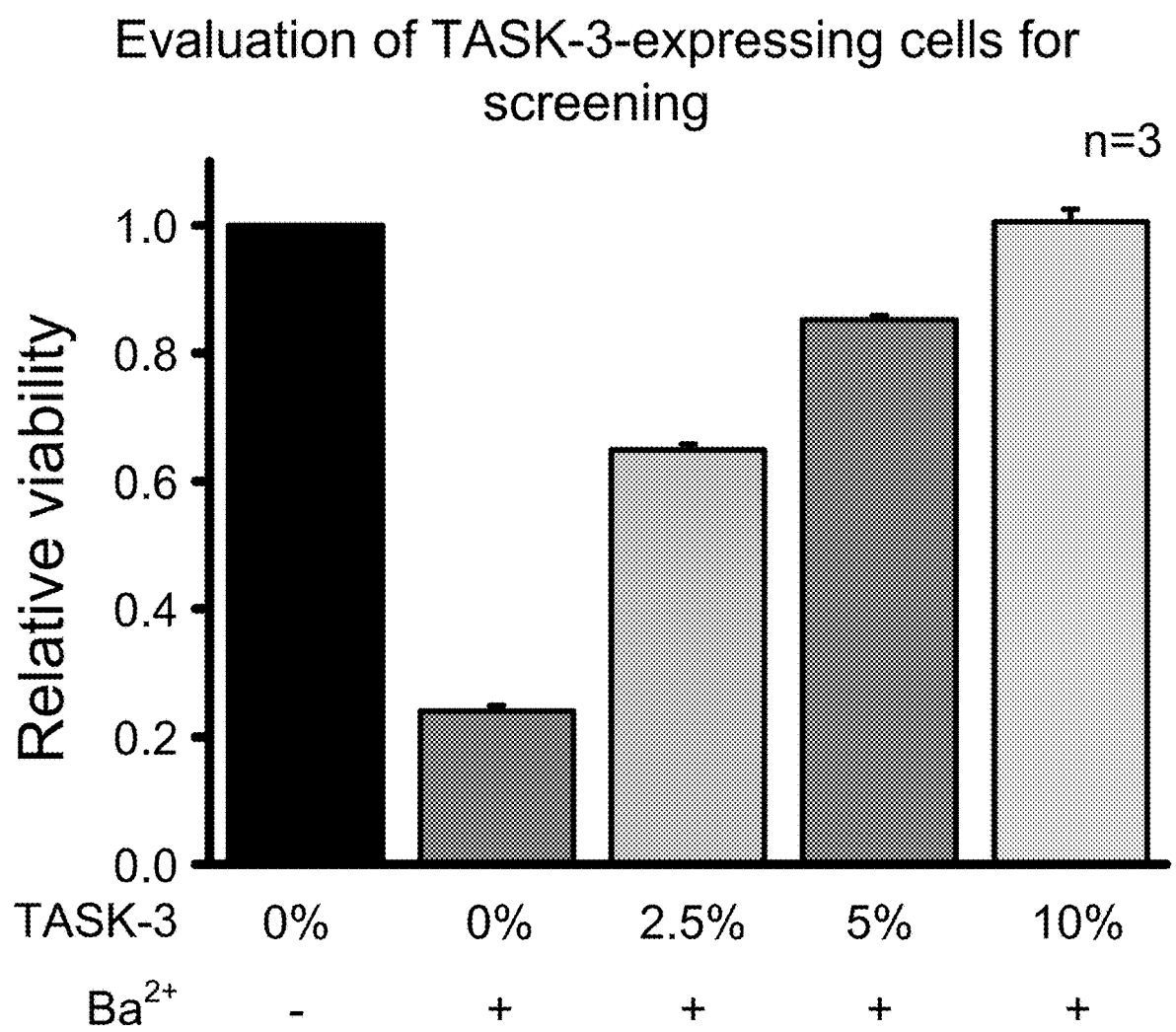
FIG. 8 is a diagram that shows the inhibition of Ba ion-inducible cell death in cells expressing TASK-3 (one type of K2P channel)

As shown in FIG. 8, the inhibitory effect on cell death by TASK-3 was observed to correlate with its amount of introduction. This fact shows that the proportion for cell death due to the administration of excess Ba ion varies when the expression level of an investigational inhibitory ion channel is adjusted. When the amount of expression is increased to at least a certain level, cell death does not reach 100% even when Kir 2.x is completely inhibited by the Ba ion. This case is suitable for screening for inhibitors of a target ion channel. The preceding thus demonstrates that, by selecting test cells in a suitable state of constant expression and by selecting a suitable Ba ion concentration, conditions can be established at which approximately 50% cell death is produced by the administration of the Ba ion and both inhibitors and agonists can be screened under conditions of maximum sensitivity.

Fifth Embodiment hSK2 and hSK4, which are each one type of human-derived Ca ion-activated ion channel, were respectively subcloned in a baculovirus vector, which is a viral vector, and were inserted into the Kir 2.1 #mutated Nav cells prepared in Second Embodiment to prepare hSK2 transiently expressing Kir 2.1+IFM/QQQ+SK2 cells (referred to herebelow as SK2 test cells) and hSK4 transiently expressing Kir 2.1+IFM/QQQ+SK4 cells (referred to herebelow as SK4 test cells). Sf-900 III SFM (Thermo Fisher Scientific) was used for the culture medium for baculovirus vector production, and Dulbecco's Modified Eagle Medium (D-MEM) culture medium supplemented with 10% fetal bovine serum (FBS) was used as the culture medium for the test cells.

Figure 9:
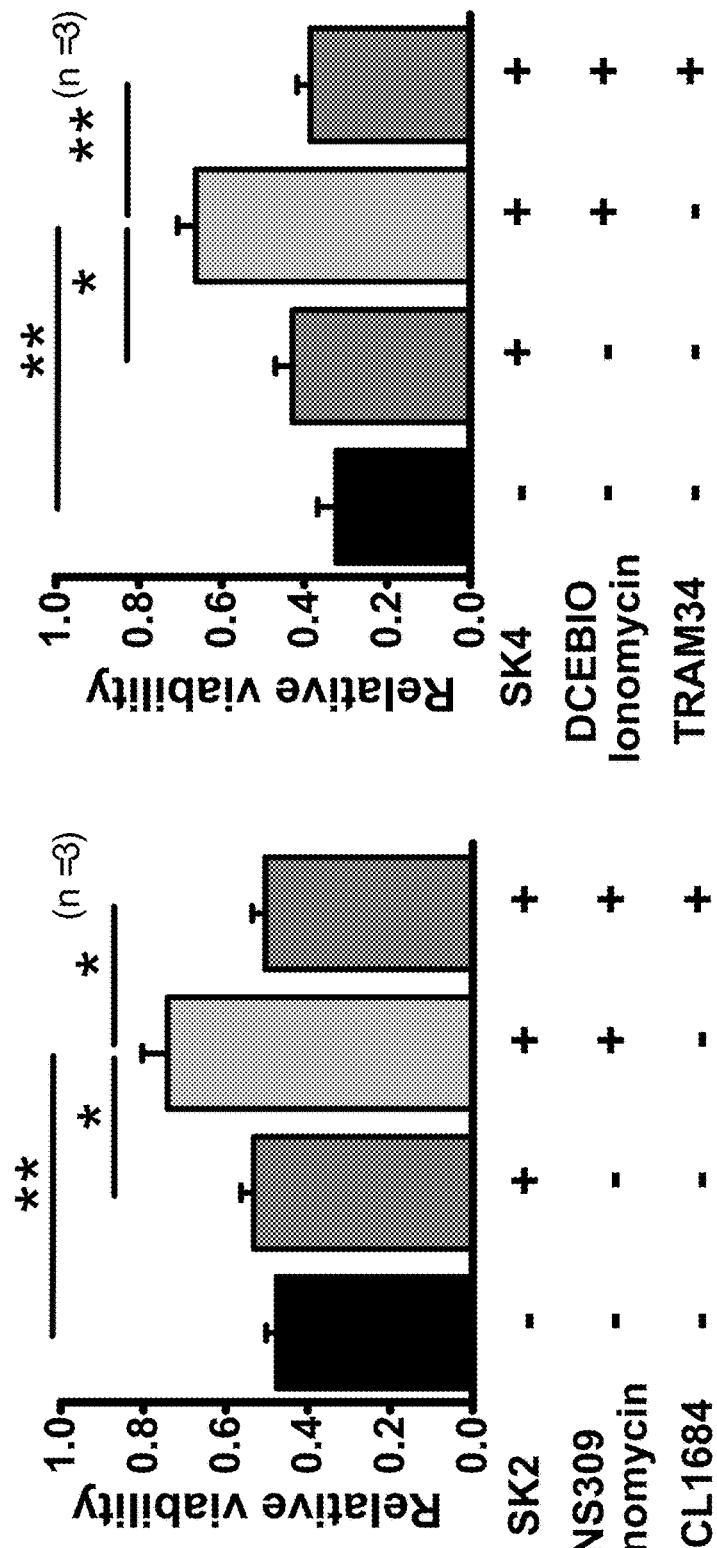
FIG. 9 is a diagram that shows the action of activators (DCEBIO, NS309) and inhibitors to the SK channel on cells expressing SK2 and cells expressing SK4.

With the SK2 test cells and SK4 test cells, the culture medium was replaced with measurement buffer; suitable additions were made of Ca ion (100 nM), SK/IK activator, SK inhibitor, and IK selective inhibitor; and culture was carried out and cell death was assayed. The results are given in FIG. 9.

As shown in FIG. 9A, cell death of the SK2 test cells was inhibited when NS309 (3-oxime-6,7-dichloro-1H-indole-2,3-dione), an SK/IK activator, was also added to the SK2 test cells in the presence of 100 nM Ca ion. That is, the action of an SK activator such as NS309 could be observed. Moreover, when both NS309, an SIC/IK activator, and UCL1684, an SK inhibitor, were added, the NS309-mediated inhibition of cell death was extinguished. The preceding thus demonstrates that, using this evaluation system, the SK ion channel can also be used as the target ion channel and in addition the action of activators and inhibitors on this ion channel can be evaluated.

As shown in FIG. 9B, cell death of the SK4 test cells was inhibited when DCEBIO (5,6-dichloro-1-ethyl-1,3-dihydro-2H-benzimidazole-2-one), an SK/IK activator, was also added to the SK4 test cells in the presence of 100 nM Ca ion. That is, the action of an SK activator such as DCEBIO could be observed. Moreover, when both DCEBIO, an SK/IK activator, and TRAM34, an IK selective inhibitor, were added, the DCEBIO-mediated inhibition of cell death was extinguished. The preceding thus demonstrates that, using this evaluation system, the SK4(IK) ion channel can also be used as the target ion channel and in addition the action of activators and inhibitors on this ion channel can be evaluated.

The present screening material has thus been demonstrated to also be suitable for ion channels other than K2P channels, for example, SK channels and the Slack channel (KCNT1) and Slick channel (KCNT2) that are sodium-activated potassium channels, and to also be usable in the search for agents that act on many other potassium channels and chloride channels.

Hereinafter, documents related to the teachings disclosed in the present specification are shown. The following documents are incorporated by reference into the present specification.

1. Alagem N, Dvir M, and Reuveny E. Mechanism of $Ba^{2+}$ block of a mouse inwardly rectifying $K^+$ channel: differential contribution by two discrete residues. J Physiol 534: 381-393, 2001.
2. Alloui A, Zimmermann K, Mamet J, Duprat F, Noel J, Chemin J, Guy N, Blondeau N, Voilley N, Rubat-Coudert C, Borsotto M, Romey G, Heurteaux C, Reeh P, Eschalier A, and Lazdunski M. TREK-1, a $K^+$ channel involved in polymodal pain perception. EMBO J 25: 2368-2376, 2006.
3. Bayliss D A and Barrett P Q. Emerging roles for two-pore-domain potassium channels and their potential therapeutic impact. Trends Pharmacol Sci 29: 566-575, 2008.
4. Blondeau N, Petrault O, Manta S, Giordanengo V, Gounon P, Bordet R, Lazdunski M, and Heurteaux C. Polyunsaturated fatty acids are cerebral vasodilators via the TREK-1 potassium channel. Circ Res 101: 176-184, 2007.
5. Borsotto M, Veyssiere J, Moha Ou Maati H, Devader C, Mazella J, and Heurteaux C. Targeting two-pore domain $K^+$ channels TREK-1 and TASK-3 for the treatment of depression: a new therapeutic concept. Br J Pharmacol 172: 771-784, 2015.
6. Campanucci V A, Brown S T, Hudasek K, O'Kelly I M, Nurse C A, and Fearon I M. O2 sensing by recombinant TWIK-related halothane-inhibitable channel-1 background K⁺ channels heterologously expressed in human embryonic kidney cells. Neuroscience 135: 1087-1094, 2005.
7. Chen L Q, Santarelli V, Horn R, and Kalien R G. A unique role for the S4 segment of domain 4 in the inactivation of sodium channels. J Gen Physiol 108: 549-556, 1996.
8. Claydon T W, Makary S Y, Dibb K M, and Boyett M R. The selectivity filter may act as the agonist-activated gate in the G protein-activated K i r 3.1/K i r 3.4 K⁺ channel. J Biol Chem 278: 50654-50663, 2003.
9. Coburn C A, Luo Y, Cui M, Wang J, Soil R, Dong J, Hu B, Lyon M A, Santarelli V P, Kraus R L, Gregan Y, Wang Y, Fox S V, Binns J, Doran S M, Reiss D R, Tannenbaum P L, Gotter A L, Meinke P T, and Renger J J. Discovery of a pharmacologically active antagonist of the two-pore-domain potassium channel K2P9.1 (TASK-3). ChemMedChem 7: 123-133, 2012.
10. Devilliers M, Busserolles J, Lolignier S, Deval E, Pereira V, Alloui A, Christin M, Mazet B, Delmas P, Noel J, Lazdunski M, and Eschalier A. Activation of TREK-1 by morphine results in analgesia without adverse side effects. Nat Commun 4: 2941, 2013.
11. Dhamoon A S, Pandit S V, Sarmast F, Parisian K R, Guha P, Li Y, Bagwe S, Taffet S M, and Anumonwo J M. Unique K i r 2.x properties determine regional and species differences in the cardiac inward rectifier K⁺ current. Circ Res 94: 1332-1339, 2004.
12. Dube E, Hermo L, Chan P T, and Cyr D G. Alterations in gene expression in the caput epididymides of nonobstructive azoospermic men. Biol Reprod 78: 342-351, 2008.
13. Ehling P, Cerina M, Budde T, Meuth S G, and Bittner S. The CNS under pathophysiologic attack—examining the role of K₂p channels. Pflugers Arch 467: 959-972, 2015.
14. Enyedi P and Czirjak G. Molecular background of leak K⁺ currents: two-pore domain potassium channels. Physiol Rev 90: 559-605, 2010.
15. Enyedi P and Czirjak G. Properties, regulation, pharmacology, and functions of the $K_{2P}$ channel, TRESK. Pflugers Arch 467: 945-958, 2015.
16. Es-Salah-Lamoureux Z, Steele D F, and Fedida D. Research into the therapeutic roles of two-pore-domain potassium channels. Trends Pharmacol Sci 31: 587-595, 2010.
17. Flaherty D P, Simpson D S, Miller M, Maki B E, Zou B, Shi J, Wu M, McManus O B, Aube J, Li M, and Golden J E. Potent and selective inhibitors of the TASK-1 potassium channel through chemical optimization of a bis-amide scaffold. Bioorg Med Chem Lett 24: 3968-3973, 2014.
18. Franks N P and Honore E. The TREK K₂p channels and their role in general anaesthesia and neuroprotection. Trends Pharmacol Sci 25: 601-608, 2004.
19. Friedrich C, Rinne S, Zumhagen S, Kiper A K, Silbernagel N, Netter M F, Stallmeyer B, Schulze-Bahr E, and Decher N. Gain-of-function mutation in TASK-4 channels and severe cardiac conduction disorder. EMBO Mol Med 6: 937-951, 2014.
20. Grant A O, Chandra R, Keller C, Carboni M, and Starmer C F. Block of wild-type and inactivation-deficient cardiac sodium channels IFM/QQQ stably expressed in mammalian cells. Biophys J 79: 3019-3035, 2000.
21. Heurteaux C, Guy N, Laigle C, Blondeau N, Duprat F, Mazzuca M, Lang-Lazdunski L, Widmann C, Zanzouri M, Romey G, and Lazdunski M. TREK-1, a K⁺ channel involved in neuroprotection and general anesthesia. EMBO J 23: 2684-2695, 2004.
22. Heurteaux C, Lucas G, Guy N, El Yacoubi M, Thummler S, Peng X D, Noble F, Blondeau N, Widmann C, Borsotto M, Gobbi G, Vaugeois J M, Debonnel G, and Lazdunski M. Deletion of the background potassium channel TREK-1 results in a depression-resistant phenotype. Nat Neurosci 9: 1134-1141, 2006.
23. Honore E. The neuronal background K2p channels: focus on TREK1. Nat Rev Neurosci 8: 251-261, 2007.
24. Kim Y, Bang H, and Kim D. TASK-3, a new member of the tandem pore K⁺ channel family. J Biol Chem 275: 9340-9347, 2000.
25. Kindler C H, Paul M, Zou H, Liu C, Winegar B D, Gray A T, and Yost C S. Amide local anesthetics potently inhibit the human tandem pore domain background K⁺ channel TASK-2 (KCNK5). J Pharmacol Exp Ther 306: 84-92, 2003.
26. Larkman P M and Perkins E M. A TASK-like pH- and amine-sensitive 'leak' K⁺ conductance regulates neonatal rat facial motoneuron excitability in vitro. Eur J Neurosci 21: 679-691, 2005.
27. Lesage F, Maingret F, and Lazdunski M. Cloning and expression of human TRAAK, a polyunsaturated fatty acids-activated and mechano-sensitive FEBS Lett 471: 137-140, 2000.
28. Lotshaw D P. Biophysical, pharmacological, and functional characteristics of cloned and native mammalian two-pore domain K⁺ channels. Cell Biochem Biophys 47: 209-256, 2007.
29. Ma X Y, Yu J M, Zhang S Z, Liu X Y, Wu B H, Wei X L, Yan J Q, Sun H L, Yan H T, and Zheng J Q. External Ba²⁺ block of the two-pore domain potassium channel TREK-1 defines conformational transition in its selectivity filter. J Biol Chem 286: 39813-39822, 2011.
30. Maingret F, Lauritzen I, Patel A J, Heurteaux C, Reyes R, Lesage F, Lazdunski M, and Honore E. TREK-1 is a heat-activated background K⁺ channel. EMBO J 19: 2483-2491, 2000.
31. McDaniel S S, Platoshyn O, Yu Y, Sweeney M, Miriel V A, Golovina V A, Krick S, Lapp B R, Wang J Y, and Yuan J X. Anorexic effect of K+ channel blockade in mesenteric arterial smooth muscle and intestinal epithelial cells. J Appl Physiol (1985) 91: 2322-2333, 2001.
32. McNulty M M, Kyle J W, Lipkind G M, and Hanck D A. An inner pore residue (Asn406) in the Nav1.5 channel controls slow inactivation and enhances mibefradil block to T-type Ca²⁺ channel levels. Mol Pharmacol 70: 1514-1523, 2006.
33. Noel J, Zimmermann K, Busserolles J, Deval E, Alloui A, Diochot S, Guy N, Borsotto M, Reeh P, Eschalier A, and Lazdunski M. The mechano-activated K⁺ channels TRAAK and TREK-1 control both warm and cold perception. EMBO J 28: 1308-1318, 2009.
34. Pandit L M, Lloyd E E, Reynolds J O, Lawrence W S, Reynolds C, Wehrens X H, and Bryan R M. TWIK-2 channel deficiency leads to pulmonary hypertension through a rho-kinase-mediated process. Hypertension 64: 1260-1265, 2014.
35. Patton D E, West J W, Catterall W A, and Goldin A L. Amino acid residues required for fast Na⁺-channel inactivation: charge neutralizations and deletions in the III-IV linker. Proc Natl Acad Sci USA 89: 10905-10909, 1992.
36. Renigunta V, Yuan H, Zuzarte M, Rinne S, Koch A, Wischmeyer E, Schlichthorl G, Gao Y, Karschin A, Jacob R, Schwappach B, Daut J, and Preisig-Muller R. The retention factor p11 confers an endoplasmic reticulum-localization signal to the potassium channel TASK-1. Traffic 7: 168-181, 2006.

37. Schmidt C, Wiedmann F, Langer C, Tristram F, Anand P, Wenzel W, Lugenbiel P, Schweizer P A, Katus H A, and Thomas D. Cloning, functional characterization, and remodeling of K2p3.1 (TASK-1) potassium channels in a porcine model of atrial fibrillation and heart failure. Heart Rhythm 11: 1798-1805, 2014.

38. Schmidt C, Wiedmann F, Voigt N, Zhou X B, Heijman J, Lang S, Albert V, Kallenberger S, Ruhparwar A, Szabo G, Kallenbach K, Karck M, Borggrefe M, Biliczki P, Ehrlich J R, Baczko I, Lugenbiel P, Schweizer P A, Donner B C, Katus H A, Dobrev D, and Thomas D. Upregulation of K2p3.1 $K^+$ Current Causes Action Potential Shortening in Patients With Chronic Atrial Fibrillation. Circulation 132: 82-92, 2015.

39. Schram G, Pourrier M, Wang Z, White M, and Nattel S. Barium block of K i r 2 and human cardiac inward rectifier currents: evidence for subunit-heteromeric contribution to native currents. Cardiovasc Res 59: 328-338, 2003.

40. Tucker S J, Gribble F M, Proks P, Trapp S, Ryder T J, Haug T, Reimann F, and Ashcroft F M. Molecular determinants of $K_{ATP}$ channel inhibition by ATP. EMBO J 17: 3290-3296, 1998.

41. West J W, Patton D E, Scheuer T, Wang Y, Goldin A L, and Catterall W A. A cluster of hydrophobic amino acid residues required for fast Na-channel inactivation. Proc Natl Acad Sci USA 89: 10910-10914, 1992.

42. Yamazaki D, Kito H, Yamamoto S, Ohya S, Yamamura H, Asai K, and Imaizumi Y. Contribution of Kir2 potassium channels to ATP-induced cell death in brain capillary endothelial cells and reconstructed HEK293 cell model. Am J Physiol Cell Physiol 300: C75-86, 2011.

43. Zou B, Flaherty D P, Simpson D S, Maki B E, Miller M R, Shi J, Wu M, McManus O B, Golden J E, Aube J, and Li M. ML365: Development of Bis-Amides as Selective Inhibitors of the KCNK3/TASK1 Two Pore Potassium Channel., Probe Reports from the NIH Molecular Libraries Program, 2010.

SEQUENCE LISTING FREE TEXT

SEQ ID Nos. 2-3: primer

The invention claimed is:

1. A method for screening for an agonist or inhibitor of a target ion channel by using cells provided with
   a voltage-dependent Na ion channel variant that prolongs the duration of an action potential associated with depolarization for 1 minute or more,
   a K ion channel that deepens the resting membrane potential in the negative direction to −50 mV or less, and
   an inhibitory target ion channel, other than the K ion channel, that contributes to deepening the resting membrane potential of the cell in the negative direction or shortening the duration of the action potential associated with depolarization and suppresses depolarization and/or death of the cells caused by supplying a selective inhibitor for the K ion channel to the cells,
   the method comprising:
   supplying the selective inhibitor for the K ion channel to the cells;
   supplying the cells with a test compound having the potential to inhibit or activate the inhibitory target ion channel under the existence of the selective inhibitor supplied;
   detecting whether the cells undergo cell death due to the supply of the test compound, wherein the detecting is performed without electrical stimulus to the cells; and
   identifying whether the test compound is an inhibitor or an activator of the target ion channel.

2. The method according to claim 1, wherein the supplying the selective inhibitor creates a state in which the depolarization and death of the cells induced by the selective inhibitor for the K ion channel is suppressed by action of the inhibitory target ion channel.

3. The method according to claim 1, wherein the inhibitory target ion channel is selected from the group consisting of a potential-dependent ion channel, a ligand-gated ion channel, a mechanical stimulation-dependent ion channel, a temperature-dependent ion channel, a leak channel ion channel, and a phosphorylation-dependent ion channel.

4. The method according to claim 1, wherein the K ion channel is at least one ion channel of an ion channel group selected from the group consisting of:
   an inwardly rectifying ion channel group selected from the group consisting of Kir2.1, Kir2.2, Kir3.X, Kir4.X, Kir5.X, Kir6.X, and Kir7.X,
   a K2P ion channel group, and
   a Ca ion activated K ion channel group.

* * * * *

SEQUENCE LISTING

```
<160> NUMBER OF SEQ ID NOS: 5

<210> SEQ ID NO 1
<211> LENGTH: 2016
<212> TYPE: PRT
<213> ORGANISM: Homo sapiens

<400> SEQUENCE: 1

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205
```

```
Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620
```

-continued

```
Glu His Pro Pro Asp Thr Thr Thr Pro Ser Glu Pro Gly Gly Pro
625                 630                 635                 640

Gln Met Leu Thr Ser Gln Ala Pro Cys Val Asp Gly Phe Glu Pro
                645                 650                 655

Gly Ala Arg Gln Arg Ala Leu Ser Ala Val Ser Val Leu Thr Ser Ala
                660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
        690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
                740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
                820                 825                 830

Gly Asn Ser Val Gly Ala Leu Gly Asn Leu Thr Leu Val Leu Ala Ile
                835                 840                 845

Ile Val Phe Ile Phe Ala Val Val Gly Met Gln Leu Phe Gly Lys Asn
850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
        995                 1000                1005

Tyr Ser Pro Pro Pro Pro Glu Thr Glu Lys Val Pro Pro Thr Arg
    1010                1015                1020

Lys Glu Thr Arg Phe Glu Glu Gly Glu Gln Pro Gly Gln Gly Thr
    1025                1030                1035
```

```
Pro Gly Asp Pro Glu Pro Val Cys Val Pro Ile Ala  Val Ala Glu
    1040                1045               1050

Ser Asp Thr Asp Asp Gln Glu Glu Asp Glu Glu Asn  Ser Leu Gly
    1055                1060               1065

Thr Glu Glu Glu Ser Ser Lys Gln Gln Glu Ser Gln  Pro Val Ser
    1070                1075               1080

Gly Gly Pro Glu Ala Pro Pro Asp Ser Arg Thr Trp  Ser Gln Val
    1085                1090               1095

Ser Ala Thr Ala Ser Ser Glu Ala Glu Ala Ser Ala  Ser Gln Ala
    1100                1105               1110

Asp Trp Arg Gln Gln Trp Lys Ala Glu Pro Gln Ala  Pro Gly Cys
    1115                1120               1125

Gly Glu Thr Pro Glu Asp Ser Cys Ser Glu Gly Ser  Thr Ala Asp
    1130                1135               1140

Met Thr Asn Thr Ala Glu Leu Leu Glu Gln Ile Pro  Asp Leu Gly
    1145                1150               1155

Gln Asp Val Lys Asp Pro Glu Asp Cys Phe Thr Glu  Gly Cys Val
    1160                1165               1170

Arg Arg Cys Pro Cys Cys Ala Val Asp Thr Thr Gln  Ala Pro Gly
    1175                1180               1185

Lys Val Trp Trp Arg Leu Arg Lys Thr Cys Tyr His  Ile Val Glu
    1190                1195               1200

His Ser Trp Phe Glu Thr Phe Ile Ile Phe Met Ile  Leu Leu Ser
    1205                1210               1215

Ser Gly Ala Leu Ala Phe Glu Asp Ile Tyr Leu Glu  Glu Arg Lys
    1220                1225               1230

Thr Ile Lys Val Leu Leu Glu Tyr Ala Asp Lys Met  Phe Thr Tyr
    1235                1240               1245

Val Phe Val Leu Glu Met Leu Leu Lys Trp Val Ala  Tyr Gly Phe
    1250                1255               1260

Lys Lys Tyr Phe Thr Asn Ala Trp Cys Trp Leu Asp  Phe Leu Ile
    1265                1270               1275

Val Asp Val Ser Leu Val Ser Leu Val Ala Asn Thr  Leu Gly Phe
    1280                1285               1290

Ala Glu Met Gly Pro Ile Lys Ser Leu Arg Thr Leu  Arg Ala Leu
    1295                1300               1305

Arg Pro Leu Arg Ala Leu Ser Arg Phe Glu Gly Met  Arg Val Val
    1310                1315               1320

Val Asn Ala Leu Val Gly Ala Ile Pro Ser Ile Met  Asn Val Leu
    1325                1330               1335

Leu Val Cys Leu Ile Phe Trp Leu Ile Phe Ser Ile  Met Gly Val
    1340                1345               1350

Asn Leu Phe Ala Gly Lys Phe Gly Arg Cys Ile Asn  Gln Thr Glu
    1355                1360               1365

Gly Asp Leu Pro Leu Asn Tyr Thr Ile Val Asn Asn  Lys Ser Gln
    1370                1375               1380

Cys Glu Ser Leu Asn Leu Thr Gly Glu Leu Tyr Trp  Thr Lys Val
    1385                1390               1395

Lys Val Asn Phe Asp Asn Val Gly Ala Gly Tyr Leu  Ala Leu Leu
    1400                1405               1410

Gln Val Ala Thr Phe Lys Gly Trp Met Asp Ile Met  Tyr Ala Ala
    1415                1420               1425
```

-continued

| | | | | | | | | | | |
|---|---|---|---|---|---|---|---|---|---|---|
|Val|Asp|Ser|Arg|Gly|Tyr|Glu|Glu|Pro|Gln|Trp|Glu|Tyr|Asn|
|1430| | | | |1435| | | |1440| |

Leu Tyr Met Tyr Ile Tyr Phe Val Ile Phe Ile Phe Gly Ser
1445                      1450                             1455

Phe Phe Thr Leu Asn Leu Phe Ile Gly Val Ile Ile Asp Asn Phe
1460                      1465                            1470

Asn Gln Gln Lys Lys Lys Leu Gly Gly Gln Asp Ile Phe Met Thr
1475                      1480                           1485

Glu Glu Gln Lys Lys Tyr Tyr Asn Ala Met Lys Lys Leu Gly Ser
1490                      1495                           1500

Lys Lys Pro Gln Lys Pro Ile Pro Arg Pro Leu Asn Lys Tyr Gln
1505                      1510                         1515

Gly Phe Ile Phe Asp Ile Val Thr Lys Gln Ala Phe Asp Val Thr
1520                      1525                         1530

Ile Met Phe Leu Ile Cys Leu Asn Met Val Thr Met Met Val Glu
1535                      1540                         1545

Thr Asp Asp Gln Ser Pro Glu Lys Ile Asn Ile Leu Ala Lys Ile
1550                      1555                         1560

Asn Leu Leu Phe Val Ala Ile Phe Thr Gly Glu Cys Ile Val Lys
1565                      1570                         1575

Leu Ala Ala Leu Arg His Tyr Tyr Phe Thr Asn Ser Trp Asn Ile
1580                      1585                         1590

Phe Asp Phe Val Val Val Ile Leu Ser Ile Val Gly Thr Val Leu
1595                      1600                         1605

Ser Asp Ile Ile Gln Lys Tyr Phe Phe Ser Pro Thr Leu Phe Arg
1610                      1615                         1620

Val Ile Arg Leu Ala Arg Ile Gly Arg Ile Leu Arg Leu Ile Arg
1625                      1630                         1635

Gly Ala Lys Gly Ile Arg Thr Leu Leu Phe Ala Leu Met Met Ser
1640                      1645                         1650

Leu Pro Ala Leu Phe Asn Ile Gly Leu Leu Leu Phe Leu Val Met
1655                      1660                         1665

Phe Ile Tyr Ser Ile Phe Gly Met Ala Asn Phe Ala Tyr Val Lys
1670                      1675                         1680

Trp Glu Ala Gly Ile Asp Asp Met Phe Asn Phe Gln Thr Phe Ala
1685                      1690                         1695

Asn Ser Met Leu Cys Leu Phe Gln Ile Thr Thr Ser Ala Gly Trp
1700                      1705                         1710

Asp Gly Leu Leu Ser Pro Ile Leu Asn Thr Gly Pro Pro Tyr Cys
1715                      1720                         1725

Asp Pro Thr Leu Pro Asn Ser Asn Gly Ser Arg Gly Asp Cys Gly
1730                      1735                         1740

Ser Pro Ala Val Gly Ile Leu Phe Phe Thr Thr Tyr Ile Ile Ile
1745                      1750                         1755

Ser Phe Leu Ile Val Val Asn Met Tyr Ile Ala Ile Ile Leu Glu
1760                      1765                         1770

Asn Phe Ser Val Ala Thr Glu Glu Ser Thr Glu Pro Leu Ser Glu
1775                      1780                         1785

Asp Asp Phe Asp Met Phe Tyr Glu Ile Trp Glu Lys Phe Asp Pro
1790                      1795                         1800

Glu Ala Thr Gln Phe Ile Glu Tyr Ser Val Leu Ser Asp Phe Ala
1805                      1810                         1815

```
Asp Ala Leu Ser Glu Pro Leu Arg Ile Ala Lys Pro Asn Gln Ile
    1820            1825                1830

Ser Leu Ile Asn Met Asp Leu Pro Met Val Ser Gly Asp Arg Ile
    1835            1840                1845

His Cys Met Asp Ile Leu Phe Ala Phe Thr Lys Arg Val Leu Gly
    1850            1855                1860

Glu Ser Gly Glu Met Asp Ala Leu Lys Ile Gln Met Glu Glu Lys
    1865            1870                1875

Phe Met Ala Ala Asn Pro Ser Lys Ile Ser Tyr Glu Pro Ile Thr
    1880            1885                1890

Thr Thr Leu Arg Arg Lys His Glu Glu Val Ser Ala Met Val Ile
    1895            1900                1905

Gln Arg Ala Phe Arg Arg His Leu Leu Gln Arg Ser Leu Lys His
    1910            1915                1920

Ala Ser Phe Leu Phe Arg Gln Gln Ala Gly Ser Gly Leu Ser Glu
    1925            1930                1935

Glu Asp Ala Pro Glu Arg Glu Gly Leu Ile Ala Tyr Val Met Ser
    1940            1945                1950

Glu Asn Phe Ser Arg Pro Leu Gly Pro Pro Ser Ser Ser Ser Ile
    1955            1960                1965

Ser Ser Thr Ser Phe Pro Pro Ser Tyr Asp Ser Val Thr Arg Ala
    1970            1975                1980

Thr Ser Asp Asn Leu Gln Val Arg Gly Ser Asp Tyr Ser His Ser
    1985            1990                1995

Glu Asp Leu Ala Asp Phe Pro Pro Ser Pro Asp Arg Asp Arg Glu
    2000            2005                2010

Ser Ile Val
    2015

<210> SEQ ID NO 2
<211> LENGTH: 40
<212> TYPE: DNA
<213> ORGANISM: Artificial
<220> FEATURE:
<223> OTHER INFORMATION: primer

<400> SEQUENCE: 2 gttaggggc caggaccaac aacagacaga ggagcagaag                                40

<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3
cttctgctcc tctgtctgtt gttggtcctg gccccctaac                               40

<210> SEQ ID NO 4
<211> LENGTH: 54
<212> TYPE: PRT
<213> ORGANISM: Homo sapiens

<400> SEQUENCE: 4

Leu Ile Ala Leu Leu His Gly Asp Leu Asp Ala Ser Lys Glu Gly Lys
1               5                   10                  15

Ala Cys Val Ser Glu Val Asn Ser Phe Thr Ala Ala Phe Leu Phe Ser
            20                  25                  30
```

-continued

```
Ile Glu Thr Gln Thr Thr Ile Gly Tyr Gly Phe Arg Cys Val Thr Asp
            35                  40                  45

Glu Cys Pro Ile Ala Val
    50

<210> SEQ ID NO 5
<211> LENGTH: 53
<212> TYPE: PRT
<213> ORGANISM: Homo sapiens

<400> SEQUENCE: 5

Ala Val Ala His Gly Asp Leu Glu Pro Ala Glu Gly Arg Gly Arg Thr
1               5                   10                  15

Pro Cys Val Met Gln Val His Gly Phe Met Ala Ala Phe Leu Phe Ser
            20                  25                  30

Ile Glu Thr Gln Thr Thr Ile Gly Tyr Gly Leu Arg Cys Val Thr Glu
            35                  40                  45

Glu Cys Pro Val Ala
    50
```